(12) United States Patent
Chacon et al.

(10) Patent No.: US 9,488,746 B2
(45) Date of Patent: *Nov. 8, 2016

(54) CAPACITIVE SENSING FOR AUTOMATED RECLINER FURNITURE

(71) Applicant: L & P Property Management Company, South Gate, CA (US)

(72) Inventors: Ryan Edward Chacon, Carthage, MO (US); William Robert Rohr, Joplin, MO (US); Avinash Madadi, Webb City, MO (US); Gregory Mark Lawson, Tupelo, MS (US)

(73) Assignee: L&P PROPERTY MANAGEMENT COMPANY, South Gate, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/608,170

(22) Filed: Jan. 28, 2015

(65) Prior Publication Data

US 2015/0137835 A1     May 21, 2015

Related U.S. Application Data

(63) Continuation-in-part of application No. 13/854,720, filed on Apr. 1, 2013, now Pat. No. 9,089,223, which is a continuation-in-part of application No. 13/749,120, filed on Jan. 24, 2013, which is a continuation-in-part of application No. 13/346,386, filed on Jan. 9, 2012.

(51) Int. Cl.
*G01R 27/26* (2006.01)
*G01V 3/08* (2006.01)
(Continued)

(52) U.S. Cl.
CPC .............. *G01V 3/08* (2013.01); *A47C 21/00* (2013.01); *G01R 27/2605* (2013.01);
(Continued)

(58) Field of Classification Search
CPC .............. A61B 5/6892; A61B 5/11; A61B 2562/0214; A61B 5/1115; A61B 5/6891; G08B 21/22; H03K 17/955; H03K 2217/96078; H03K 2017/9602; A47C 21/00; A47C 20/08; G01R 27/26; G01R 27/2605; G01V 3/08; G01V 3/088; A61G 7/015
USPC ........................................ 324/658, 663, 686
See application file for complete search history.

(56) References Cited

U.S. PATENT DOCUMENTS 3,372,319 A   3/1968   Rhodes
3,971,371 A   7/1976   Bloom
(Continued)

FOREIGN PATENT DOCUMENTS

EP   1275328 A1   1/2003
WO   9944179 A1   9/1999
WO   0211585 A1   2/2002

OTHER PUBLICATIONS

Non-Final Office Action dated Apr. 28, 2015 in U.S. Appl. No. 13/749,120, 15 pages.
(Continued)

*Primary Examiner* — Amy He
(74) *Attorney, Agent, or Firm* — Shook, Hardy & Bacon L.L.P.

(57) ABSTRACT

A system and method for incorporating occupancy-detecting technology into furniture is provided. More particularly, the invention relates to detecting occupancy in a recliner using a sinuous wire detection array incorporated into a seat. Further embodiments of the invention are directed to a system and method for incorporating capacitance detection technology with one or more conductive features of a recliner mechanism. In some aspects, a sensor is provided based on coupling one or more conductive features to a control component of the capacitance detector control component. A controller may determine the corresponding response based on occupancy detection and/or presence detection. A processor may receive information regarding changes in capacitance and determines when a change in voltage satisfies a threshold. Based on a determination of occupancy and/or presence, a variety of corresponding features of the adjustable recliner may be activated.

18 Claims, 26 Drawing Sheets

(51) Int. Cl.
  *A47C 21/00* (2006.01)
  *H03K 17/955* (2006.01)
  *H03K 17/96* (2006.01)
  *A61G 7/015* (2006.01)
  *A61B 5/00* (2006.01)
  *A61B 5/11* (2006.01)

(52) U.S. Cl.
  CPC ........... *G01V 3/088* (2013.01); *H03K 17/955* (2013.01); *A61B 5/1115* (2013.01); *A61B 5/6891* (2013.01); *A61G 7/015* (2013.01); *H03K 2017/9602* (2013.01); *H03K 2217/96078* (2013.01)

(56) References Cited

U.S. PATENT DOCUMENTS

| | | | |
|---|---|---|---|
| 3,991,746 | A | 11/1976 | Hanna et al. |
| 5,235,319 | A | 8/1993 | Hill |
| 5,260,666 | A | 11/1993 | Dishman et al. |
| 5,481,769 | A | 1/1996 | Schneider |
| 6,025,782 | A | 2/2000 | Newham |
| 6,067,019 | A | 5/2000 | Scott |
| 6,283,504 | B1 | 9/2001 | Stanley et al. |
| 6,768,420 | B2 | 7/2004 | McCarthy et al. |
| 6,946,853 | B2 | 9/2005 | Gifford et al. |
| 7,135,983 | B2 | 11/2006 | Filippov et al. |
| 7,190,277 | B2 | 3/2007 | Fultz et al. |
| 8,397,324 | B2 | 3/2013 | Hayes et al. |
| 8,427,450 | B2 | 4/2013 | Lin |
| 2002/0070866 | A1 | 6/2002 | Newham |
| 2003/0011225 | A1 | 1/2003 | Barcesat |
| 2005/0088264 | A1 | 4/2005 | Iwasaki |
| 2005/0231379 | A1 | 10/2005 | Sprecher et al. |
| 2006/0164254 | A1 | 7/2006 | Kamizono et al. |
| 2006/0261769 | A1 | 11/2006 | Rees |
| 2007/0040676 | A1 | 2/2007 | Bandringa et al. |
| 2009/0119841 | A1 | 5/2009 | Takashima |
| 2009/0211818 | A1 | 8/2009 | Kondo et al. |
| 2010/0096899 | A1 | 4/2010 | Kato et al. |
| 2011/0209287 | A1 | 9/2011 | Call et al. |
| 2011/0221459 | A1 | 9/2011 | Uno et al. |
| 2012/0025991 | A1 | 2/2012 | O'Keefe et al. |
| 2013/0174343 | A1 | 7/2013 | Chacon et al. |
| 2013/0176040 | A1 | 7/2013 | Rohr et al. |
| 2013/0247302 | A1 | 9/2013 | Chacon et al. |

OTHER PUBLICATIONS

Non-Final Office Action dated Apr. 29, 2015 in U.S. Appl. No. 13/346,386, 9 pages.
International Search Report and Written Opinion dated May 16, 2014 in Application No. PCT/US2014/12797, 9 pages.
Non-Final Office Action dated Jul. 7, 2014 in U.S. Appl. No. 13/749,120, 21 pages.
International Search Report with Written Opinion dated Aug. 29, 2014 in Application No. PCT/US2014/32555, 8 pages.
Non-Final Office Action dated Nov. 20, 2014 in U.S. Appl. No. 13/854,720, 12 pages.
Final Office Action dated Dec. 15, 2014 in U.S. Appl. No. 13/346,386, 21 pages.
Final Office Action dated Dec. 18, 2014 in U.S. Appl. No. 13/749,120, 19 pages.
Notice of Allowance dated Mar. 20, 2015 in U.S. Appl. No. 13/854,720, 8 pages.
Non Final Office Action dated Jun. 19, 2014 in U.S. Appl. No. 13/346,386, 17 pages.
International Preliminary Report on Patentability dated Aug. 6, 2015 in Application No. PCT/US2014/012797, 7 pages.
Final Office Action dated Sep. 28, 2015 in U.S. Appl. No. 13/346,386, 9 pages.
International Preliminary Report on Patentability dated Oct. 15, 2015 in Application No. PCT/US14/32555, 7 pages.
Final Office Action dated Oct. 28, 2015 in U.S. Appl. No. 13/749,120, 16 pages.
Notice of Allowance dated Jan. 8, 2016 in U.S. Appl. No. 13/346,386, 10 pages.
International Search Report with Written Opinion dated Jun. 10, 2016 in PCT Application No. PCT/US2016/015358, 14 pages.
Ex Parte Quayle Office Action dated May 26, 2016 in U.S. Appl. No. 13/749,120, 7 pages.
Notice of Allowance dated Jun. 15, 2016 in U.S. Pat. No. 4,608,173, 9 pages.
European Search Report dated Aug. 9, 2016 in European Patent Application No. 14743295.9, 7 pages.
Notice of Allowance dated Aug. 12, 2016 in U.S. Appl. No. 13/749,120, 8 pages.

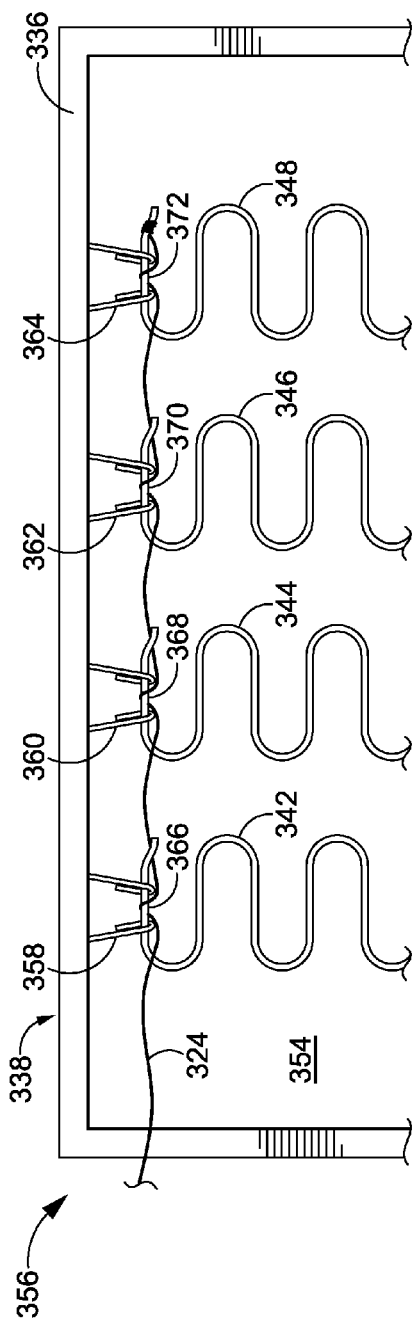
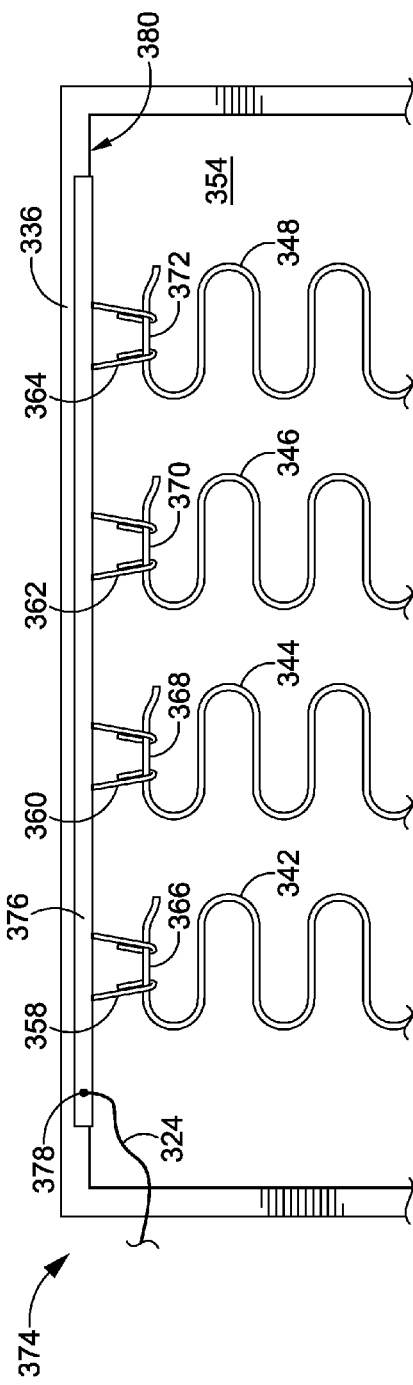
FIG. 37A
FIG. 37B

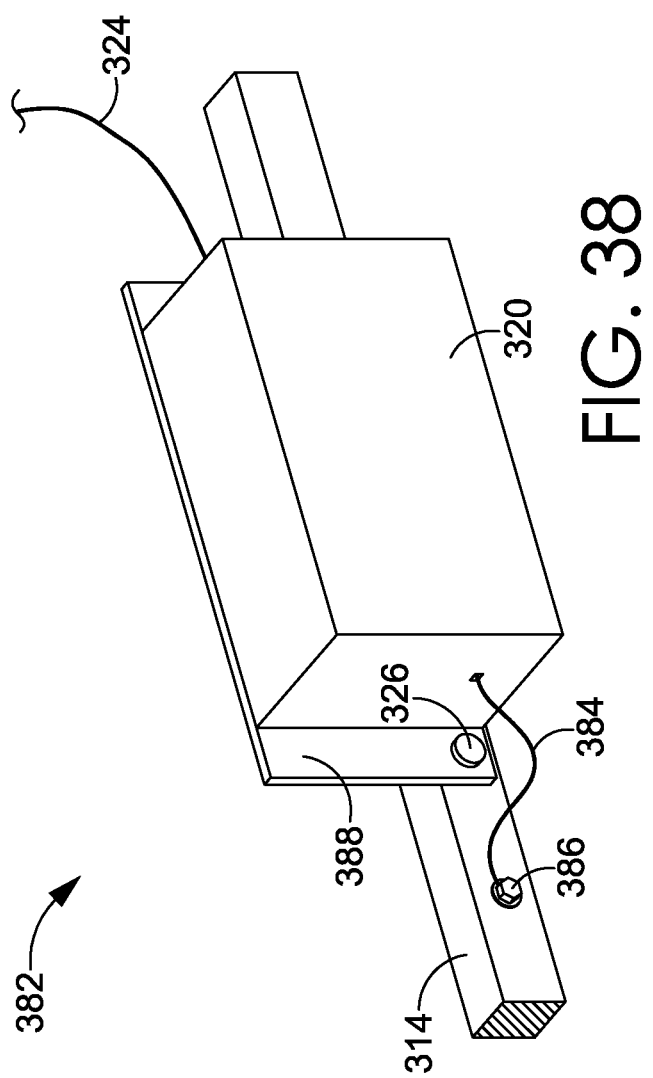

CAPACITIVE SENSING FOR AUTOMATED RECLINER FURNITURE

CROSS-REFERENCE TO RELATED APPLICATIONS

This application is a continuation-in-part of U.S. Nonprovisional patent application Ser. No. 13/854,720, filed Apr. 1, 2013, entitled "Occupancy Detection for Furniture," which is a continuation-in-part of U.S. Nonprovisional patent application Ser. No. 13/749,120, filed Jan. 24, 2013, entitled "Capacitive Wire Sensing for Furniture," which is a continuation-in-part of U.S. Nonprovisional patent application Ser. No. 13/346,386, filed Jan. 9, 2012, entitled "Capacitive Wire Sensing for Furniture". The entire content of all three applications is hereby incorporated by reference. This application is also related by subject matter to co-pending U.S. Nonprovisional patent application Ser. No. 14/608,173, filed Jan. 28, 2015, entitled "Occupancy Detection for Automated Recliner Furniture," , the entire content of which is hereby incorporated by reference.

STATEMENT REGARDING FEDERALLY SPONSORED RESEARCH OR DEVELOPMENT

Not applicable.

TECHNICAL FIELD

The present invention generally relates to occupancy-detecting and presence-sensing technology incorporated into furniture. More particularly, the invention relates to coordinating capacitive technology and controller features for automated furniture items, such as bedding systems, recliners, automated recliners, lift chairs, and other automated furniture items, for detecting the presence of an occupant and synchronizing related features and/or accessories.

BACKGROUND OF THE INVENTION

Traditional occupancy-detection technology does not automatically pair to automated bedding system controllers and accessories. As such, incorporating occupancy detection technology into existing automated bedding systems may be challenging. Further, without an integrated occupancy-detection system, a consumer may not have access to control particular features and/or accessories with the automated bedding system, particularly those features/accessories that are primarily controlled through manual manipulation or programming.

Occupancy detection systems utilizing pressure sensors and/or mechanical triggers may not easily integrate into automated furniture items, such as automated recliners and lift chairs. Further, presence detection systems associated with automated recliners or lift chairs may generate a false indication of presence while monitoring multiple sources and/or types of detection devices. Accordingly, a need exists for a reliable occupancy-detection technology for use with furniture, such as an automated bedding system, which addresses the foregoing and other problems.

BRIEF SUMMARY OF THE INVENTION

The present invention generally relates to a system and method for occupancy detection and/or presence detection that incorporates a capacitive component into furniture items, including automated bedding systems, recliner furniture, lift chairs, and the like. It should be understood that the invention contemplates incorporating an automatic occupancy-detection component and/or system into a variety of furniture items, both bedding and otherwise, and that the invention is not limited to the specific item for which occupancy detection is provided. Additionally, the present invention is described as detecting/sensing occupancy (e.g., the presence of a person or other being in or on the automated furniture item) using exemplary components such as a detection pad, a detection grid, a series of detection pads, a control cable, and/or a processor. Although a final determination of presence may be conducted using a processor and/or software associated with the claimed system/apparatus, reference to occupancy sensing and/or detection "by" the system/apparatus, or a determination thereof by the processor, is not meant to be limiting. For example, a conductive signal detected by a detection pad may be processed by software associated with a processor in a control enclosure, and such processing may result in a final determination of occupancy. In other words, a detection pad could be described as having "detected" occupancy, even though the detection determination was ultimately made in software associated with a processor. Similarly, a conductive signal detected via a capacitive component, such as a presence sensing frame of an automated recliner, could be described as having "detected" presence even though the presence detection was ultimately made via software associated with a computing device having a processor.

In one embodiment, one or more capacitive detection pads are secured to a portion of a top and/or bottom surface of a platform of an adjustable bed. In another embodiment, a wire grid is coupled to a top and/or bottom surface of an adjustable bed platform. A series of interconnected, capacitive tape strips may also be coupled to a top and/or bottom surface of an adjustable bed platform. In further embodiments, a detection pad may be incorporated into a topper material of a mattress. In some embodiments, a single occupant position may be detected using an array of multiple detection pads.

Exemplary embodiments of the invention include a control enclosure coupled to a capacitive component (such as a detection pad or other detection material) that is associated with a processor that receives presence-detecting data via the capacitive component. Software associated with the control enclosure and the detection pad may then make a determination of occupancy of the bedding system. Based on a determination of occupancy, or lack thereof, a corresponding feature of the automated bedding system may be activated.

One illustrative embodiment of an occupancy detection system includes a control component associated with an automated furniture item, the control component comprising a receiving component and a determining component; a detection array component coupled to the automated furniture item, the detection array component comprising: (1) one or more sinuous wires coupled to the automated furniture item, and (2) one or more bridging components coupled to the one or more sinuous wires and the control component, wherein the one or more bridging components are configured to generate a capacitive array associated with the one or more sinuous wires, said capacitive array configured to monitor a change in capacitance with respect to the detection array component.

In another illustrative embodiment, a method for detecting occupancy with respect to a seating surface, the method comprising receiving capacitance monitoring data from a sinuous wire detection array coupled to the item of furniture, wherein the sinuous wire detection array comprises a plurality of sinuous wires coupled to at least a portion of the seating surface and at least one bridging component coupled to the plurality of sinuous wires, wherein receiving information comprises receiving an indication of a change voltage via the sinuous wire detection array, and further wherein the sinuous wire detection array is adapted to have a voltage based on proximity of an object to the sinuous wire detection array. The method further includes determining that the change in voltage satisfies a threshold, wherein determining that the change in voltage satisfies a threshold comprises: (1) monitoring changes in voltage detected by the sinuous wire detection array over a particular period of time; and (2) comparing the change in voltage over the period of time with the threshold.

A third illustrative embodiment is directed to an occupancy detection mechanism comprising: a plurality of sinuous wires associated with a support feature of a furniture item, each of the plurality of sinuous wires comprising a conductive material configured to carry a charge; a bridging component coupled to each of the plurality of sinuous wires to provide a sinuous wire detection array, wherein the sinuous wire detection array is configured to monitor a change in capacitance detected by the sinuous wire detection array; and a control component coupled to the sinuous wire detection array, wherein the control component is configured to receive data associated with the monitored change in capacitance, wherein the sinuous wire detection array is adapted to have a voltage based on proximity of an object to one or more of the plurality of sinuous wires.

Additional objects, advantages, and novel features of the invention will be set forth in part in the description which follows, and in part will become apparent to those skilled in the art upon examination of the following, or may be learned by practice of the invention.

BRIEF DESCRIPTION OF SEVERAL VIEWS OF THE DRAWING

The present invention is described in detail below with reference to the attached drawing figures, wherein:

FIG. 37A is a bottom view of a sinuous wire support of a furniture seat, in accordance with embodiments of the invention;

FIG. 37B is a bottom view of the sinuous wire support of FIG. 37A with a foil tape coupled to the seat frame, in accordance with an embodiment of the invention;

FIG. 38 is a perspective view of a control component for an automated recliner, in accordance with embodiments of the invention;

DETAILED DESCRIPTION OF THE INVENTION

Figure 1:
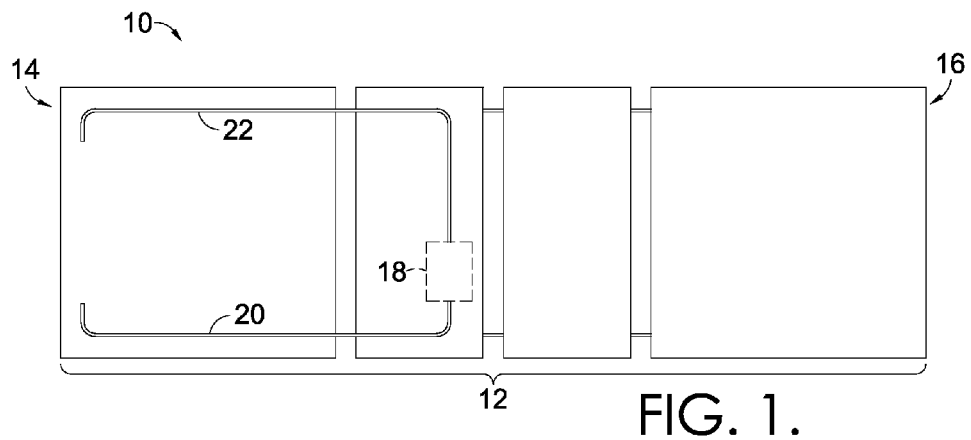
FIG. 1 is a top view of a capacitive wire coupled to the panels of an automated bed platform, in accordance with embodiments of the invention.

An embodiment of an automated bedding system 10 with capacitive wire sensing is seen in FIGS. 1-6. Referring first to FIG. 1, a top view of the platform of the automated bedding system 10 includes a plurality of panels 12 having a first end 14 and a second end 16, a control enclosure 18 (mounted below the panels 12), a first segment 20 of a capacitive wire, and a second segment 22 of a capacitive wire. In some embodiments, the first end 14 may be referred to as the "head" of the bed, while the second end 16 may be referred to as the "foot" of the bed.

When viewed from the top in FIG. 1, capacitive wiring is generally arranged near the first end 14 of the automated bedding system 10. A capacitive component, such as a capacitive wire, is adapted to have a voltage based on proximity of an object to the capacitive component. In some embodiments, the capacitive wire segments are standard conductive copper wires. The capacitance measured across such wires may be monitored by a processor that uses software to generate a determination of presence detection. In one embodiment, the Microchip® brand capacitive sensor may be used to determine when presence is detected. As such, while presence detection relies on the juxtaposition of a person or body with respect to the capacitive wiring, a determination of the level of detection or the measurement of presence is conducted digitally, in software associated with the processor.

As shown in FIG. 1, the capacitive wiring first and second segments 20 and 22 are coupled to the control enclosure 18, which is mounted below the panels 12 of the bedding system 10. In some embodiments, first and second segments 20 and 22 are made from a single capacitive wire, while in other embodiments, two separate capacitive wire segments 20 and 22 are coupled to the control enclosure 18. As will be understood, additional capacitive components, such as capacitive wire segments, may be coupled to the control enclosure 18, and arranged on the top of the plurality of panels 12. For example, additional capacitive wires arranged perpendicular to each other may be coupled to the control enclosure 18. In further embodiments, first and second segments 20 and 22 are made from a capacitive material other than wire.

Capacitive wire segments 20 and 22 may be used to detect the presence or absence of a person or other being on top of the automated bedding system 10. For example, as arranged near first end 14 of the automated bedding system 10, the torso of a person positioned on the top of the automated bedding system 10 may be detected by capacitive wire segments 20 and 22. In embodiments, capacitive wire segments 20 and 22 create a defined sensing area on the top half of the head of the bedding system 10 and are less susceptible to noise interference from articulation of the rest of the automated bedding system 10.

Figure 2:
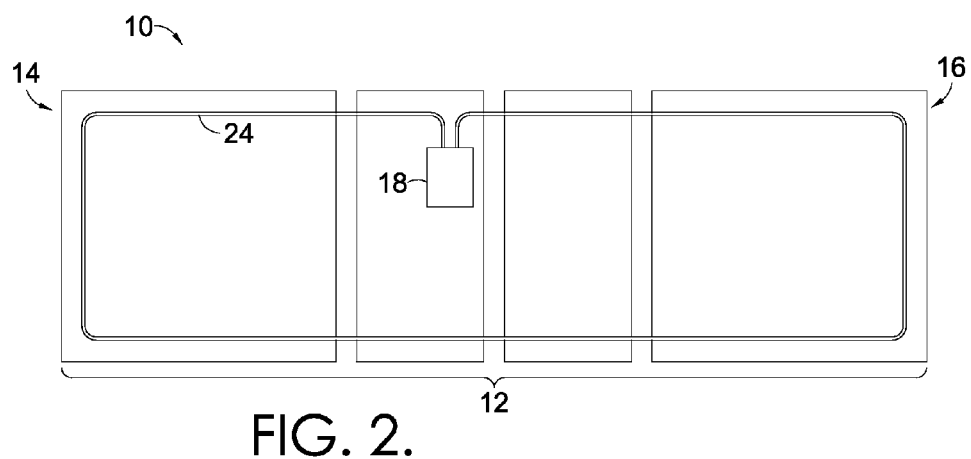
FIG. 2 is a bottom view of the automated bed platform of FIG. 1, with a capacitive wire and a control enclosure coupled to the panels, in accordance with embodiments of the invention.

Referring next to FIG. 2, a bottom view of the platform of the automated bedding system 10 includes the plurality of panels 12 having a first end 14 and a second end 16, a control enclosure 18, and a third segment 24 of capacitive wire. As shown in FIG. 2, the capacitive wiring third segment 24 is coupled to the control enclosure 18, which is mounted below the panels 12. In further embodiments, the control enclosure may be mounted in a different location on the bedding system 10 or may be external to the bedding system 10.

In some embodiments, third segment 24 is made from a single capacitive wire, while in other embodiments, multiple capacitive wire segments are coupled to the control enclosure 18. As will be understood, additional capacitive components, such as capacitive wire segments, may be coupled to the control enclosure 18 and arranged on the bottom of the plurality of panels 12. For example, additional capacitive wires arranged perpendicular to each other may be coupled to the control enclosure 18. In further embodiments, third segment 24 is made from a capacitive material other than wire.

Capacitive wire segment 24 may be used to detect the presence or absence of a person or other being below the automated bedding system 10. For example, as arranged around the perimeter of the bed at both the first and second ends 14 and 16, a person or other body underneath the automated bedding system 10 may be detected by capacitive wire segment 24. In embodiments, based on detecting presence underneath the bedding system 10, bed articulation may be stopped. As viewed from the side in FIG. 3, the first and second segments 20 and 22 (hidden from view) create a defined sensing area on the top of the platform, near the first end 14, while the third segment 24 creates a defined sensing area on the bottom of the platform of the bedding system 10.

Figure 3:
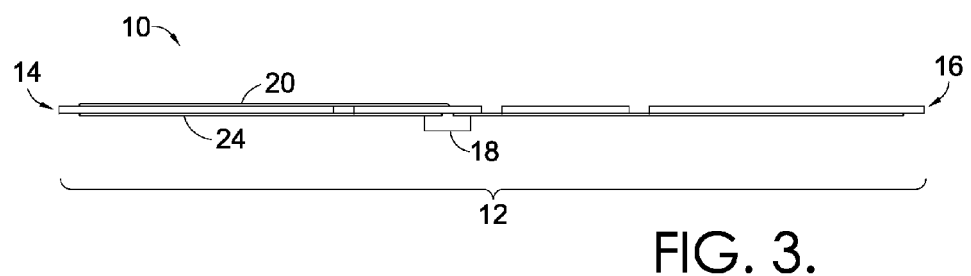
FIG. 3 is a side view of the automated bed platform of FIG. 1, with a capacitive wire coupled to the top and bottom of the platform, and the control enclosure coupled to the bottom of the platform, in accordance with embodiments of the invention.
Figure 4:
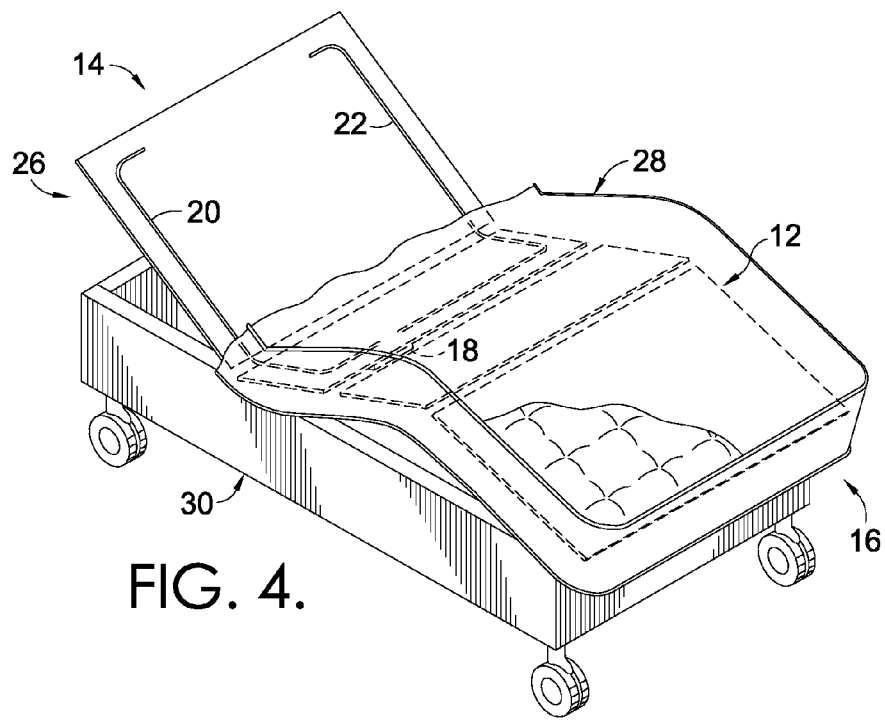
FIG. 4 is a perspective view of an automated bed with a portion of the mattress cut away to reveal the capacitive wire coupled to the top of the platform, in accordance with embodiments of the invention.

Referring next to FIG. 4, an adjustable bed 26 incorporates the automated bedding system 10 described with respect to FIGS. 1-3. The adjustable bed 26 includes a mattress 28 and a frame 30. A top portion of the mattress is cut away to reveal the first end 14 of the automated bedding system 10 platform, with the head of the bed partially raised. As described with reference to FIG. 1, capacitive wire segments 20 and 22 provide a defined sensing area near the first end 14, which detects a change in capacitance above the bed, such as the capacitance detected from a person resting on the bed.

Figure 5:
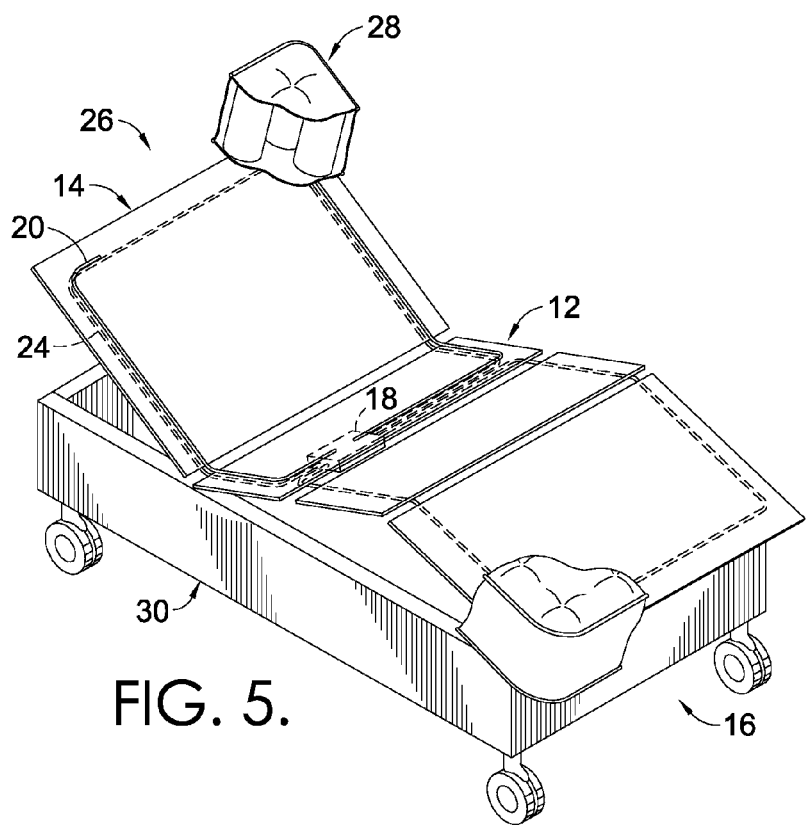
FIG. 5 is a perspective view of the automated bed of FIG. 4, with the mattress cut away to reveal the capacitive wire coupled to the top of the platform, and hidden lines indicating the capacitive wire and control enclosure coupled to the bottom of the platform, in accordance with embodiments of the invention.
Figure 6:
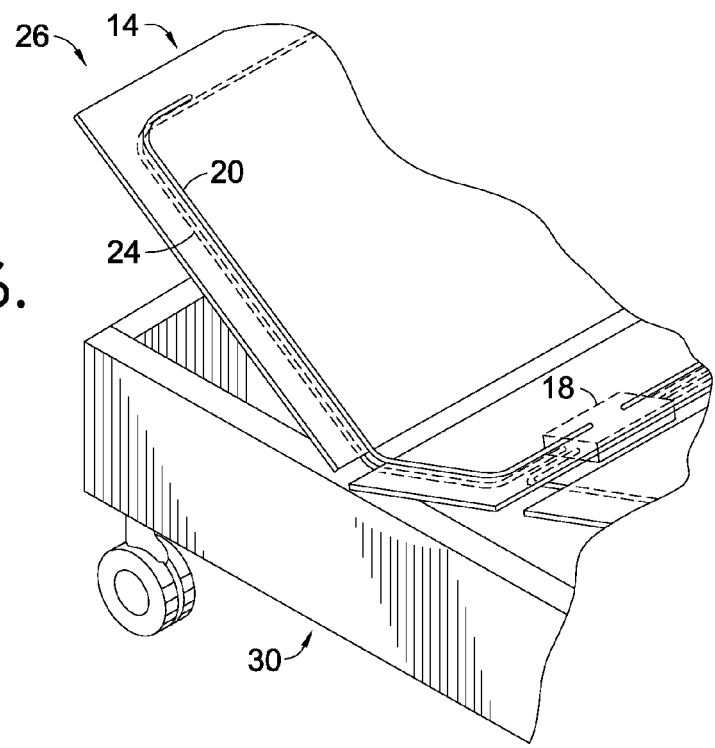
FIG. 6 is an enlarged, perspective view of the automated bed of FIG. 5, with a capacitive wire coupled to the top of the platform and hidden lines indicating the capacitive wire and control enclosure coupled to the bottom of the platform, in accordance with embodiments of the invention.

FIG. 5 depicts the adjustable bed 26 from FIG. 4 with a majority of the mattress 28 removed. As can be seen on the plurality of panels 12, first and second segments 20 and 22 of capacitive wire detect presence above the platform (e.g., on top of the mattress), while the third segment 24 detects presence below the platform (e.g., under the bed). An enlarged view of FIG. 5 is shown in FIG. 6, with hidden lines depicting capacitive wires 20 and 24 coupled to the control enclosure 18, which is mounted beneath the panels 12.

In some embodiments, in addition or alternative to positioning of capacitive wiring around the perimeter of the panels 12 that support an adjustable mattress, conductive wire is attached around the perimeter of the mattress itself. As shown in the adjustable bed 32 of FIG. 7, conductive wire may be incorporated into the tape edge surrounding the mattress 28. As such, the attached conductive wire may work as a sensor to detect presence of a person or other body near the perimeter of the mattress 28. For example, a conductive wire may be incorporated into the top tape edge 34 around the top surface of the mattress 28. In another example, a conductive wire may be incorporated into the bottom tape edge 36 around the bottom surface of the mattress 28. During manufacturing, a conductive wire may be inserted into the tape edge automatically, as the tape edge is applied to a mattress covering. In some embodiments, when routed through the tape edge perimeter, the sensitivity of the conductive wire may be adjusted in software associated with a processor used to determine presence detection.

The capacitive wire may be routed through some or all of the tape edge around the perimeter of a mattress 28. Additionally, a tape edge may be applied to both the top and bottom edges of the mattress 28, and both the top and bottom tape edges 34 and 36 may include a capacitive wire. Accordingly, the sensitivity of the capacitive wire in the top tape edge 34 may be adjusted independently from the tape edge 36 surrounding the perimeter of the bottom of the mattress. For example, a small change in voltage detected by the capacitive wires in the top tape edge 34 of the mattress may indicate that a user has moved on the surface of the mattress but is still on the bed. By contrast, a small change in voltage detected by the capacitive wires in the bottom tape edge 36 of the mattress may indicate that a person, or other being, is below the bed. In either case, different features associated with the automated bedding system 10 may be activated based on whether presence is detected above the bed (via capacitive wires in the top tape edge 34) or below the bed (via capacitive wires in the bottom tape edge 36).

Figure 7:
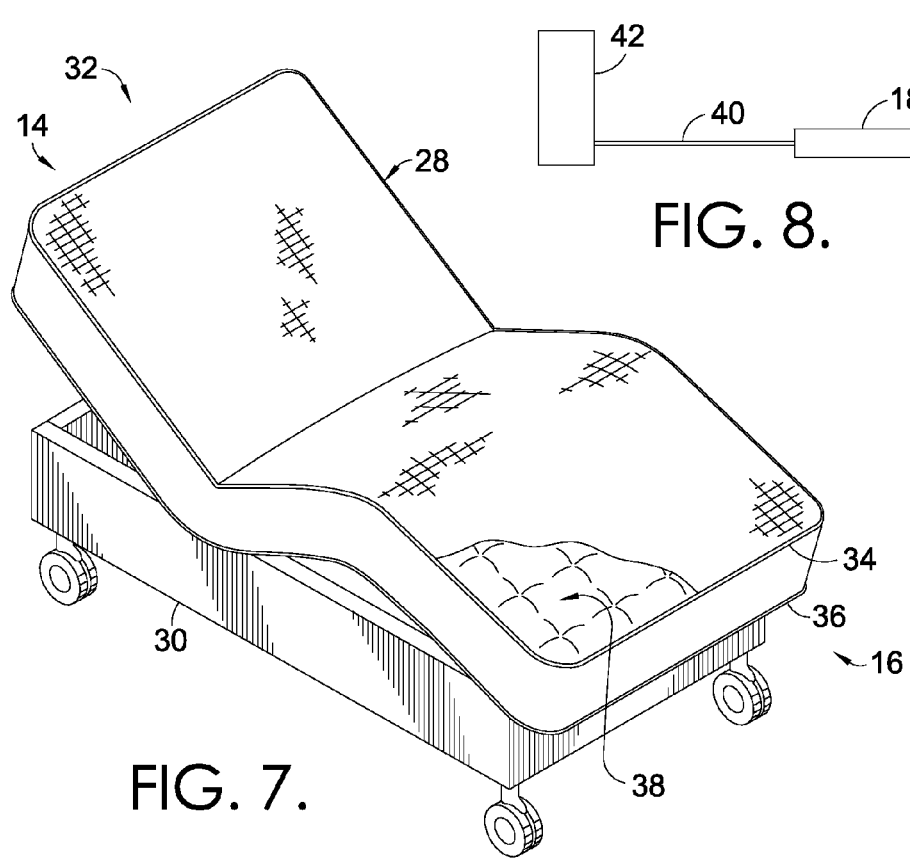
FIG. 7 is a perspective view of an automated bed with a capacitive wire incorporated into the tape edge of the mattress cover, in accordance with embodiments of the invention.

In further embodiments, a capacitive component may be incorporated into the mattress covering 38 of a mattress 28, as shown in FIG. 7. In particular, a capacitive thread may be sewn into the ticking on top of the mattress covering 38, as part of a sewn pattern. During manufacturing, a particular needle threaded with capacitive thread may be activated automatically and independently to incorporate the capacitive wire into a particular configuration on the surface of the mattress covering 38. For example, the capacitive thread may be sewn around a perimeter of the top surface of the mattress 28. In another example, the capacitive wire may be sewn in a pattern that creates perpendicular runs for capacitive detection. In one embodiment, capacitive thread sewn into the surface of a mattress covering 38 may terminate at a particular point and attach to a control enclosure 18. For example, an attachment may be used to crimp the mattress covering 38 material during sewing, to provide an attachment point for connecting the capacitive thread to a processor.

In some embodiments, a capacitive component may be incorporated into a platform-style bed. For example, a lower portion of a bed that does not articulate, such as a box spring or a mattress frame 30, may include a capacitive component that detects presence from above. In one embodiment, a capacitive wire is attached in a loop around the perimeter of the top of the frame 30, in FIG. 7. When a person or body is detected on top of the platform and/or frame 30, the articulating mattress 28 may discontinue lowering into contact with the frame 30. In one embodiment, a capacitive wire may be incorporated into the upholstery of a decorative surround (immovable frame). The sensitivity of the capacitive wire may be decreased so that direct contact is required with the edge of the surround before presence may be detected, in order to prevent false readings from a body approaching the frame and/or surround. In one embodiment, a decorative surround may include a conductive, metalized tape, such as an aluminum tape, that serves as a capacitive component for detecting presence with respect to the decorative surround. For example, a conductive, metalized tape may be adhered to a perimeter of the decorative surround of an adjustable bed to determine presence near and/or on the bed, based on a change in capacitance detected by the metalized tape.

Figure 8:
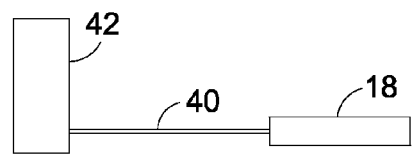
FIG. 8 is a side view of a capacitive wire coupled to a control enclosure and an inner spring of a mattress, in accordance with embodiments of the invention.

Presence may also be detected using a loop of capacitive wire incorporated inside a mattress. For example, as shown in FIG. 8, a fourth segment 40 of capacitive wire may be incorporated inside an inner spring 42 and coupled to the control enclosure 18. While only one inner spring 42 is shown, it should be understood that capacitive wire could be incorporated into one or more of the many inner springs that make up a traditional mattress. As such, the loop of capacitive wire can detect a person or object in proximity to the loop, such as a person on the mattress, above the loop of capacitive wire.

A defined sensing area is created by the routing of a capacitive wire around a perimeter of a furniture item in a variety of configurations, such as those described above. For example, a capacitive wire routed around the perimeter of a mattress, such as in the tape edge around a perimeter of the top surface of a mattress, creates a defined sensing area on the area of the mattress surrounded by the sensing perimeter. As such, a person's presence within the sensing area may be detected by the capacitive wire, which a processor may use to determine when a person exits or enters a bed. A processor coupled to the capacitive component may be housed in a control enclosure, such as control enclosure 18. In one embodiment, the control enclosure 18 is mounted below the platform of an automated bedding system 10. In further embodiments, the control enclosure 18 is mounted generally beneath the mattress 28.

In embodiments, capacitive wire incorporated into the perimeter of a mattress is used to monitor a change in capacitance over a specified amount of time. The capacitive component (capacitive wire) is adapted to have a voltage based on proximity of an object to the capacitive component. Such voltage information is collected via the capacitive component and received by the processor, which determines when a change in voltage satisfies a threshold. Once a particular change in capacitance satisfies a threshold, a corresponding function associated with the automated bed may be initiated. In embodiments, a threshold for initiating a corresponding function includes a particular amount of change in voltage within a particular amount of time. For example, when using capacitance information to turn lights on/off, a particular amount of change in voltage may be required during a particular amount of time before satisfying the threshold indicating that a person has exited the bed (and before the lights may be turned on). Similarly, a particular threshold value of voltage change may be required by the processor, over a particular amount of time, before making a determination that a person has re-entered the bed (and before the lights can be turned off again). In embodiments, a processor continuously receives capacitance monitoring information, monitors how quickly a change in capacitance occurs (how quickly the delta changes) to determine if a big enough change has occurred in a certain amount of time to satisfy a threshold, and triggers the corresponding function.

Based on satisfying a particular threshold, various features associated with the automated bedding system 10 may be activated and/or enabled. For example, an alarm clock may only be triggered if a person's presence is detected in the bed (i.e., if a threshold amount of change in voltage is detected during capacitance monitoring over a particular amount of time). In another example, additional bedding features may be activated based on presence detection by capacitive wires. Such additional integrated bedding features include having a massage motor activated to wake up a user. If a user is not present in the bed, and therefore not detected using the capacitive wires, the lack of presence detection will prevent the massage motor from running at a particular scheduled time.

A variety of other functions of the automated bedding system 10 may be controlled based on detection with a capacitive wire. In other words, a processor coupled to the capacitive wire may initiate a variety of functions based on received data indicating presence or lack of presence, as determined using capacitance information. Different functions may be controlled, such as stopping a bed from articulating when presence is detected beneath the bed, turning on/off lights based on a person exiting/entering a bed, and controlling other accessories or electrical/household appliances through internal circuitry associated with the processor. In one example, after presence is no longer detected in the bed (thereby indicating that a person has exited the bed), lights may be turned on. Additionally, when the person returns to the bed, the lights may turn off.

A variety of communication protocols may be used to control the variety of functions described above. For example, a two-way controller using ZigBee® wireless communication protocol may be used. In some embodiments, a two-way communication protocol intended for use in automation (similar to Bluetooth®) may be utilized. One embodiment of the invention may be controlled by an external sensor only, with all of the components necessary for the sensor that plug into an existing motor. In another embodiment, two separate microcontrollers may be used: one dedicated primarily for sensing purposes that, when it detects something, sends a signal to a secondary device/microcontroller that is programmed to initiate the corresponding response.

Figure 9:
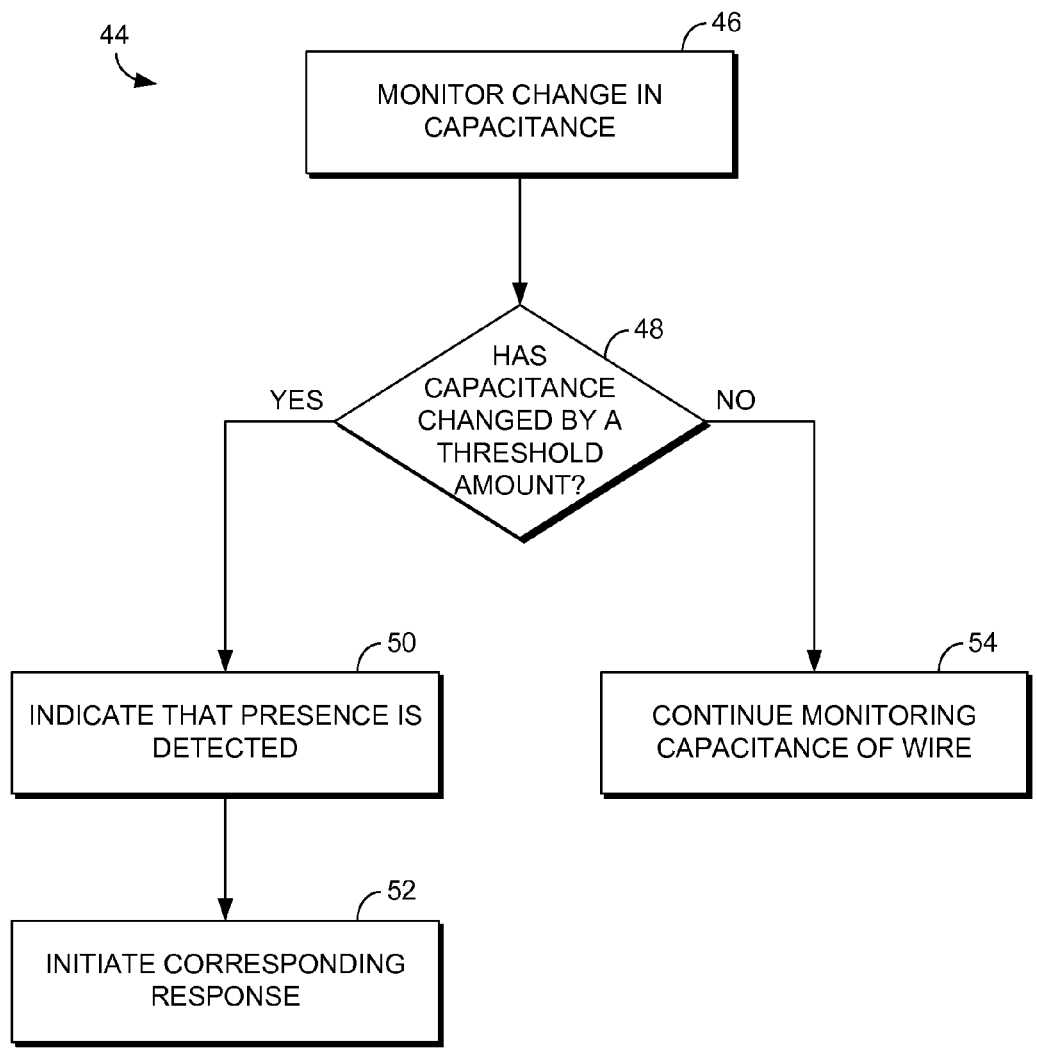
FIG. 9 is a flow diagram of an exemplary method of detecting presence with respect to a bed, in accordance with embodiments of the invention.

Turning now to FIG. 9, an exemplary flow diagram 44 depicts monitoring capacitance and making a determination of presence with respect to a furniture item. At block 46, an average change in capacitance is monitored using a capacitive wire. As discussed above, the change in capacitance indicates a change in voltage over a particular amount of time. At block 48, a determination is made regarding whether the capacitance has changed by a threshold amount. If a determination is made that the capacitance has changed by a threshold amount (i.e., a particular amount of change in voltage has occurred within a particular window of time), then an indication is made that presence has been detected at block 50, and the corresponding response is initiated at block 52. As will be understood, blocks 50 and 52 may, in some embodiments, be combined into a single step of initiation of the corresponding response based on a determination of presence detection. At block 54, if capacitance has not changed by a threshold amount, capacitance monitoring continues.

Figure 10:
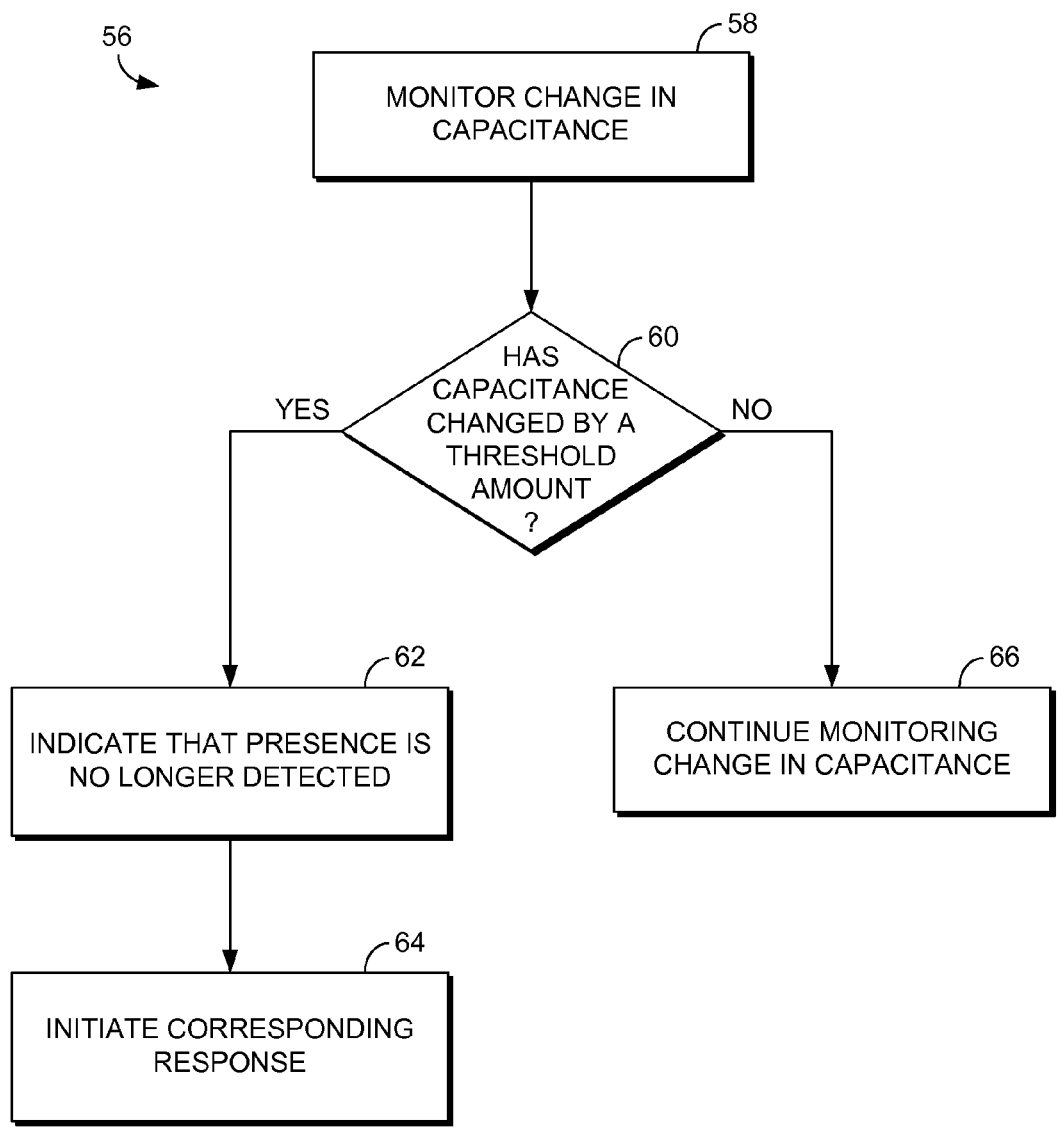
FIG. 10 is a flow diagram of an exemplary method of detecting presence with respect to a bed, in accordance with embodiments of the invention.

With reference next to FIG. 10, an exemplary flow diagram 56 depicts monitoring capacitance and making a determination that presence is no longer detected with respect to a furniture item. At block 58, an average change in capacitance is monitored using a capacitive wire. At block 60, a determination is made whether capacitance has changed by a threshold amount. At block 62, if capacitance has changed by a threshold amount, an indication that presence is no longer detected is made at block 62, and a corresponding response is initiated at block 64. At block 66, if it is determined that the threshold amount has not been satisfied, capacitance monitoring continues.

Figure 11:
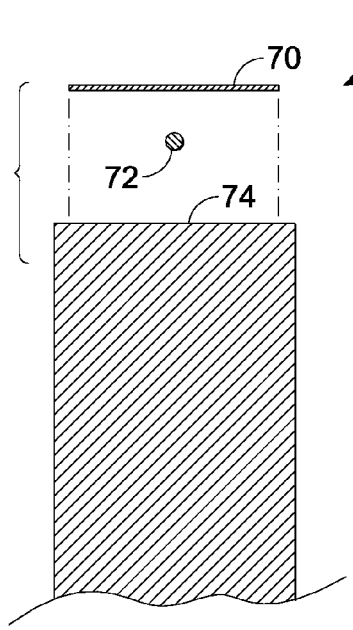
FIG. 11 is a side view of foil tape and capacitive wire for application to a substrate, in accordance with embodiments of the invention.
Figure 12:
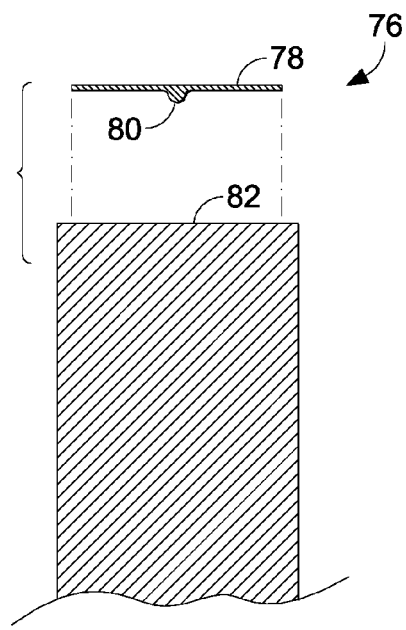
FIG. 12 is a side view of foil tape having an embedded capacitive wire for application to a substrate; in accordance with embodiments of the invention.

Referring now to FIG. 11, an exemplary capacitive sensing system 68 includes a thin-gauge foil tape 70, a thin-gauge capacitive wire 72, and a substrate 74. In embodiments, foil tape 70 attaches capacitive wire 72 to a substrate 74, such as a perimeter of an item of motion furniture or an adjustable bed. FIG. 12 depicts another exemplary capacitive sensing system 76, with a thin-gauge foil tape 78 having a thin-gauge, capacitive embedded wire 80, for attaching to a substrate 82. For example, a thin-gauge, foil tape 78 embedded with a capacitive embedded wire 80 may be held to a substrate 82, such as an adjustable bed. In embodiments, capacitive wire 72 and/or capacitive embedded wire 80 may be coupled to substrates 74 and 82 using an adhesive portion of foil tape 70 and 78. Additionally, foil tapes 70 and 78 may be pressure sensitive adhesive (PSA) foil tapes, for attaching to substrates 74 and 82. In further embodiments, thin-gauge foil tape 70 and 78 are used to attach capacitive wire 72 and/or capacitive embedded wire 80 to a substrate. In addition or alternative to attaching capacitive wire 72 or capacitive embedded wire 80 using foil tape, such capacitive wiring systems may be coupled to a substrate using staples, glue, adhesive, or otherwise fastened to a number of surfaces to create a capacitive circuit on the adjustable bed or motion furniture item.

Figure 13:
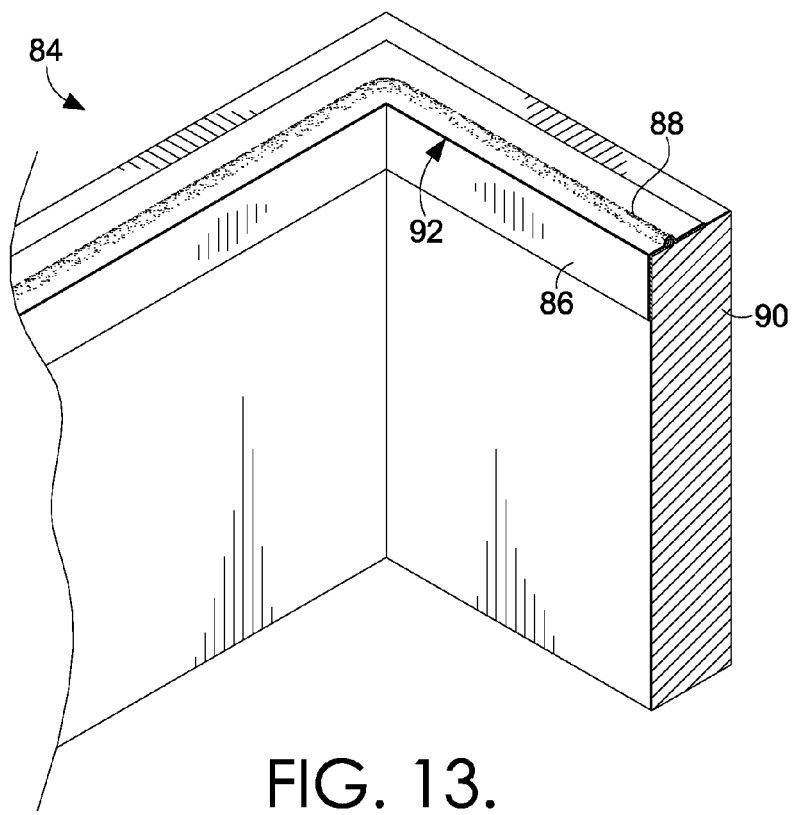
FIG. 13 is a perspective view of a foil tape having an embedded capacitive wire, applied to an edge of a substrate, in accordance with embodiments of the invention.

In the example of FIG. 13, a capacitive sensing system 84 includes a thin-gauge foil tape 86 with an embedded wire 88 coupled to a substrate 90. In particular, the foil tape 86 is applied to an inner edge 92 of substrate 90, such as an inner edge of an adjustable bed frame. In embodiments, foil tape 86 is a PSA tape that is adapted to adhere to a surface of substrate 90, while permitting the foil tape 86 (and the embedded wire 88) to maintain a charge during monitoring of capacitance. For example, foil tape 86 may be coupled to a controller and monitored using a software application that analyzes changes in capacitance, as detected via the foil tape 86 and the embedded wire 88. For example, foil tape 86 may be coupled to a controller (such as a microcontroller) associated with a software application, and used to capacitively detect mammalian touch in components such as doors, windows, furniture, or other items of moveable furniture, such as an adjustable bed. In embodiments, foil tape 86 is capacitive and is coupled to the embedded wire 88 that is electrically coupled to the microcontroller.

Figure 14:
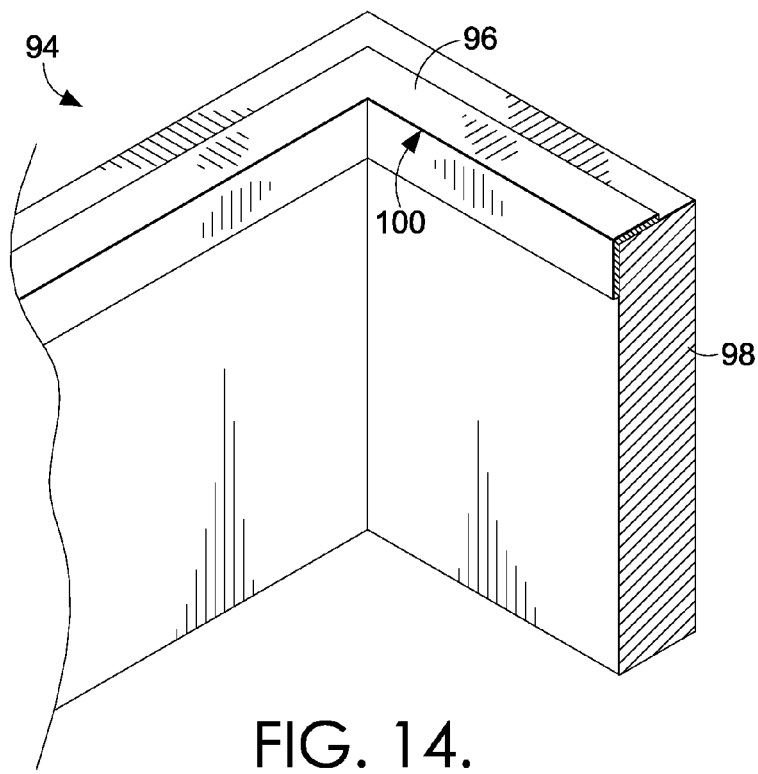
FIG. 14 is a perspective view of a foil tape applied to an edge of a substrate, in accordance with embodiments of the invention.
Figure 15:
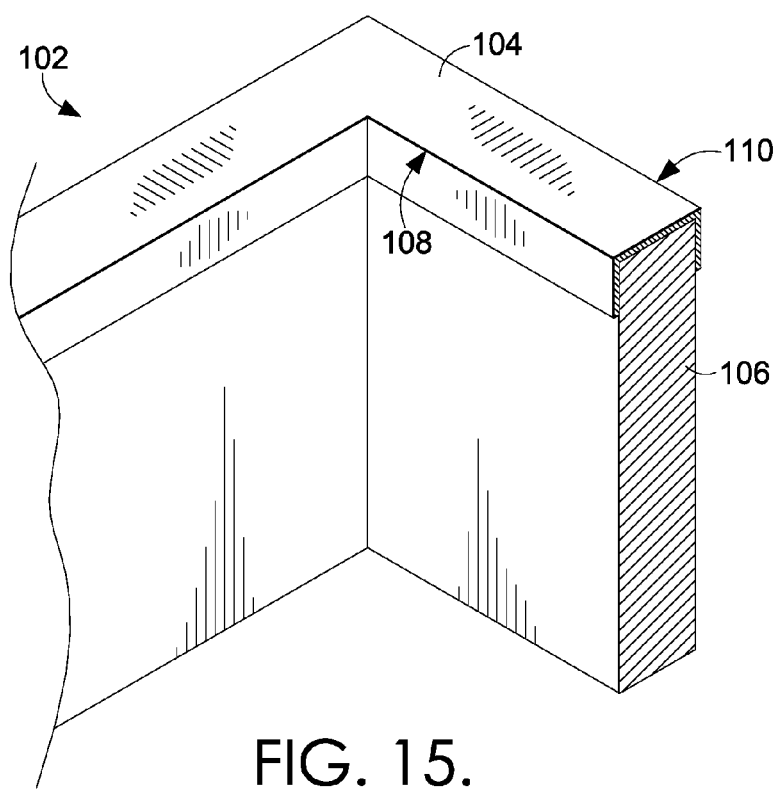
FIG. 15 is a perspective view of a foil tape applied to multiple edges of a substrate, in accordance with embodiments of the invention.

In FIG. 14, a capacitive sensing system 94 includes a capacitive cap 96 coupled to a substrate 98 along an inner edge 100. In embodiments, substrate 98 may be a frame and/or base of an adjustable bed, with an inner edge 100, on which capacitive cap 96 is applied and used for capacitive detection. In one embodiment, capacitive cap 96 is a sensing material, such as a metalized tape, that is able to detect changes in capacitance and can be placed under or on top of fabrics. Similarly, with reference to FIG. 15, capacitive sensing system 102 depicts a capacitive cap 104 coupled to the top of substrate 106. In particular, capacitive cap 104 is applied along inner edge 108 and outer edge 110. In one embodiment, capacitive cap 104 is a foil and/or metalized tape that can detect a change in capacitance. In further embodiments, substrate 106 may be a frame and/or base of an adjustable bed, with the inner edge 108 and outer edge 110, on which capacitive cap 104 may be used to detect presence based on a change in capacitance detected by the capacitive cap 104. In some embodiments, capacitive cap 96 and/or capacitive cap 104 may be a metallic coated plastic trim that can be used as a sensing material, in addition to or alternative to a conductive wire and/or foil tape. In further embodiments, capacitive caps 96 and 104 may be made from other ferrous or metallic shapes, such as angles, zees, tees, caps, etc. As such, in embodiments using foil tape for capacitive detection, additional metallic materials could be used to provide capacitive detection of presence with respect to an adjustable bed.

In embodiments, a thin-gauge perimeter wire may be installed around a perimeter of an adjustable bed and/or frame of an adjustable bed. In embodiments, the thin-gauge perimeter wire may be coupled to the base of an adjustable bed using tape; adhesives; fasteners; staples; or may be embedded or extruded through foam; covered in a thin foil tape; or attached via one or more additional/alternative hardware mechanisms. In one embodiment, the perimeter wire may be embedded in foil tape prior to application to the bedding device, as in the example of FIGS. 12-13. In a further embodiment, the perimeter wire may be connected to a coaxial cable using sockets, such as using an RCA jack and socket, or a mechanism such as a Molex® or an Amp connector.

In embodiments, the foil tape and the perimeter wire are capacitively coupled and sensitive to touch. That is, similar to the capacitive wire segments used to detect the presence or absence of a person or other being on top of an automated bedding system, foil tape and a perimeter wire coupled to a frame or base of an adjustable bed may also be capacitively coupled and able to detect presence or absence based on a detected change in capacitance. Further, such capacitance detection may be adjusted to a required amount of sensitivity for presence detection, such as "fine tuning" the microcontroller and/or software for detection using thicker upholstery.

In a further embodiment of the invention, ports, grommets, and/or sockets are added to an automated bedding mattress construction to allow connection of a capacitive wire to springs of a mattress assembly, thereby creating a capacitive array internal to the mattress. As discussed with reference to FIG. 8, capacitive wire may be incorporated into one or more inner springs of a mattress. Further, in one example, a perimeter wire coupled to an automated bed frame may also be coupled to the inner spring of a mattress assembly to create a capacitive array that detects presence with relation to both the mattress and the frame. In some embodiments, a wire mesh, such as netting and/or a screen, may be capacitively connected to a capacitive sensing system for detection associated with the same perimeter wire.

In some embodiments, body capacitance can be used to operate different types of switches as a capacitive touch sensor will respond to close-proximity detection of a change in capacitance. Accordingly, the tip of a finger may be detected by a capacitive sensor, with a minimal amount of pressure (i.e., triggered without forceful touching), and the capacitive sensing system of an automated furniture item may detect minimal amounts of bodily contact.

Figure 16:
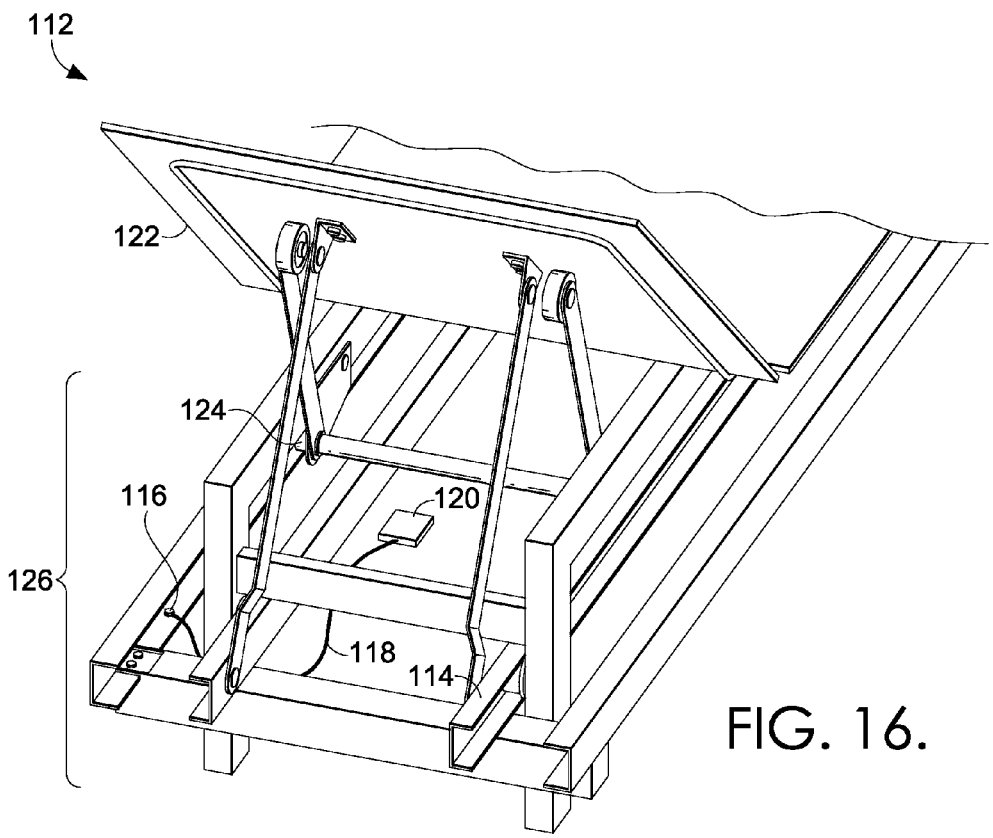
FIG. 16 is a rear perspective view of an adjustable bed, in accordance with embodiments of the invention.

Turning next to FIG. 16, a rear-perspective view of an adjustable bed 112 includes a metal, adjustable bed frame 114 coupled at a contact point 116 to a coaxial cable (coax) 118 and a controller 120. As a portion 122 of the adjustable bed 112 is in motion, presence near the frame 114 of the adjustable bed 112 may be detected by the controller 120, based on the capacitance monitored via bed frame 114. Accordingly, the metal, adjustable bed frame 114 is used as a sensor, with the metal being a conductive material adapted to carry a charge. In embodiments, multiple metal components 126 are coupled together to form the adjustable bed frame 114. Many of these parts are coupled together at joints 124 that are also adapted to carry a charge, which enables the controller 120 to detect presence with respect to contact with any conductive portion of the adjustable bed frame 114. As will be understood, embodiments discussed with reference to FIG. 16 may also be implemented in additional moveable furniture items, such as chairs.

In one embodiment, when a person contacts the adjustable bed frame 114, the frame's normal capacitance is increased. In response to the increase in capacitance by contact with the bed frame 114, the controller 120 measures the change in capacitance of the bed frame 114 against a known capacitance of the frame. In embodiments, controller 120 may be mounted to the bed frame 114 directly, with a separate microcontroller for a sensor and a separate microcontroller for controlling the bed motion. Accordingly, a sensing microcontroller may use separate channels for wire detection of presence (discussed above) and frame detection of presence. In embodiments, the use of a coax 118 to directly connect the bed frame 114 to the controller 120 reduces the amount of interference caused during monitoring and/or detection, as the coax 118 exits the controller 120 and will not detect any signals until it reaches the bed frame 114.

In one example, as connected to the bed frame 114 via coax 118, controller 120 measures capacitance by pulsing the bed frame 114 with a voltage, such as a low voltage having a minimal amount of current. In between pulses from the controller 120, the signal fed into the controller's analog to digital converter (ADC) is used to measure how much the voltage changes over time. In one embodiment, one microcontroller of the controller 120 may send out a charge, with the resulting charge being read by another microcontroller having a processor that monitors how quickly the detected charge decays. In one embodiment, when a body is in contact with the frame, the controller 120 monitors how quickly the change in capacitance rises and how far the change in capacitance rises.

Based on detection of a change in capacitance by the controller 120, the actuator of the adjustable bed frame 114 may be disabled during a motion operation if it is determined that human contact is detected. In embodiments, the controller 120 may monitor the overall levels of capacitance of the bed frame 114 to determine what changes in capacitance do and do not satisfy a threshold for determining that contact has been made. For example, the rate of change and the amount of change may be monitored to determine whether a threshold for contact has been met, and whether the travel of the bed frame 114 should be altered. In embodiments, when triggered by a controller 120, the actuators of an adjustable bed 112 may be programmed to stop all motion (such as downward motion) when contact is detected by the conductive, metal bed frame 114. In such an example, when presence of a human is detected underneath a moving, adjustable bed 112, the detection by bed frame 114 may indicate to the controller 120 to discontinue travel of the bed frame 114. In another embodiment, in response to detection of a human underneath a moving, adjustable bed 114, the actuators may reverse and/or retract motion by a particular distance, such as backing up an inch if the bed frame 114 was lowering to a downward position when presence was detected.

Accordingly, to restart travel once a condition has been met for stopping travel by the controller 120, a user may indicate to the adjustable bed 112 that 1) the condition that triggered the indication of presence has gone away, and/or 2) that the user has again selected motion of the adjustable bed frame 114 by providing an indication to the controller 120 (such as pushing a button on a controller of the adjustable bed 112). In further embodiments, controller 120 may track the usage of an adjustable bed 112 and the subsequent commands received after detecting presence near a moving bed frame 114. Such tracking may be used to designate specific actions required by the bed in response to presence detection, such as moving of a bed into a fully upright position, or discontinuing motion of the bed prior to initiating a subsequent lowering once presence is no longer detected.

Figures 17A, 17B, 17C:
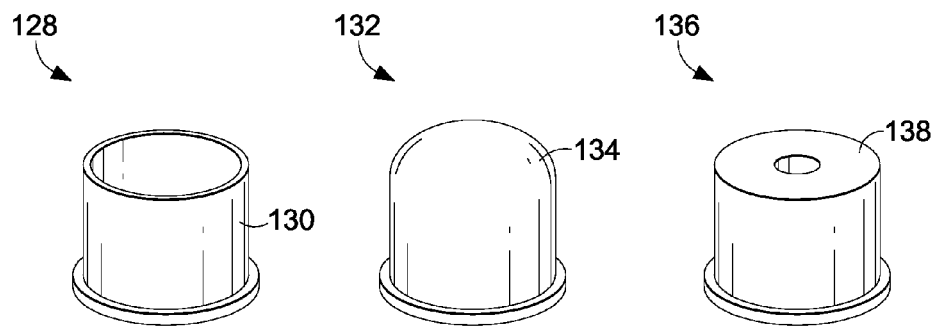
FIG. 17A is a conductive bushing, in accordance with embodiments of the invention.
FIG. 17B is a conductive encapsulating torque tube, in accordance with embodiments of the invention.
FIG. 17C is a conductive bushing, in accordance with embodiments of the invention.

With reference to FIG. 17A, an exemplary metallic bushing 128, such as conductive bushing 130, may be used to provide an acceptable transfer of energy within a metal assembly, such as the metal, adjustable bed frame 114 of FIG. 16. For example, one or more parts of an adjustable bed frame 114 may be coupled together at joints 124 that use conductive bushing 130 to carry a charge, thereby enabling a controller 120 to detect presence with respect to contact with any conductive portion of the adjustable bed frame 114. Additional embodiments of metallic bushings 132 and 136 are depicted in FIGS. 17B and 17C. FIG. 17B depicts an exemplary, conductive encapsulating torque tube 134, while FIG. 17C depicts an exemplary conductive bushing 138 for use with capacitive detection associated with a metallic assembly. Accordingly, in some embodiments, conductive bushings are made using conductive materials to create "conductive" plastics, such as using stainless steel, carbon fibers, carbon black, carbon powder, graphite, and the like. In another embodiment, conductive bushings are made using chemical additives or coatings added to plastic bushings to increase the conductivity. In further embodiments, a metal coating on the outside of a bushing, or a metal coating encapsulated inside a plastic bushing, may be used to generate conductive bushings. As will be understood, a number of metallic, conductive, and/or chemical additives, treatments, or materials may be used to create conductive bushings for use in a metallic assembly that carries a charge and is used to detect capacitance, such as a metallic, adjustable bed frame 114.

As will be understood, "traditional" bushings used in adjustable beds or motion furniture are often made with electrically insulating acetals, which prevent the transfer of a charge during detection of capacitance. Accordingly, in some embodiments, parasitic capacitive coupling may be used to capacitively couple components of the adjustable bed or motion furniture metallic assemblies. In a further embodiment, jumper wires are used to connect components of an adjustable bed that are electrically isolated due to non-conductive bushings. For example, electrically isolated parts of a metal, adjustable bed frame may be coupled to other conductive portions of the bed frame using jumper wires.

In embodiments, bushings and other washer materials being carbon-fiber filled acetal with moderate surface conductivity may be used. Such bushings and washers may assist in the transfer of energy throughout a metal, adjustable bed frame 114, its components, and related assemblies. In some embodiments, a metallic bed frame may be capacitively coupled to other assemblies in the adjustable base. Accordingly, the term "metallic assembly" may be used to refer to any of the frame, components of the frame, and assemblies of an adjustable furniture item, such as a bed.

In one embodiment, acetal carbon-fiber filled bushings are less than or equal to the surface resistivity of 1.0E+3 ohm and have a volume resistivity of 1.0E+3 ohm centimeter (using test methods per IEC 60093). The human body capacitance is the input to the metallic assembly, and the carbon-fiber filled bushings act as "jumper wires" to transmit energy between the metallic assemblies in adjustable beds and motion furniture. In one embodiment, electroceramics (ceramic materials specifically formulated for electrical properties) may be tailored for use as a highly conductive bushing material, such as the electronically conductive ceramic consisting of Indium Tin Oxide (ITO), Lamthanum-doped strontium titanate (SLT), and yttrium-doped strontium titanate (SYT).

Figure 18:
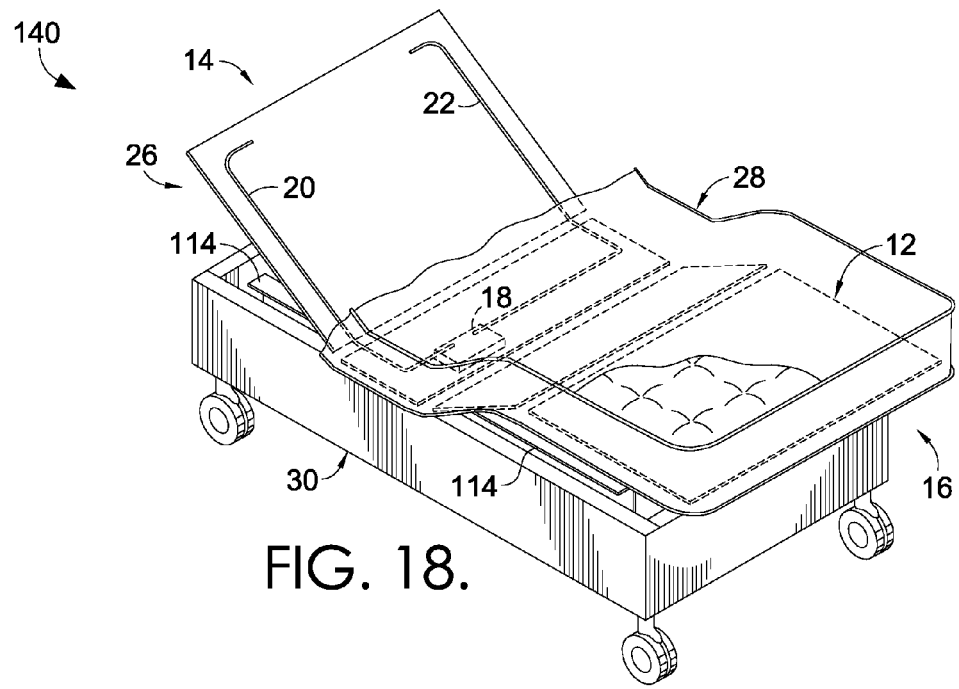
FIG. 18 is a perspective view of an automated bed with head and feet portions of the bed raised to partially reveal a metal, adjustable bed frame, and a portion of the mattress cut away to reveal capacitive wire coupled to the top of the platform, in accordance with embodiments of the invention.

Turning next to FIG. 18, an automated bedding system 140 includes an adjustable bed 26 having a plurality of panels 12 with a first end 14 and a second end 16, a control enclosure 18 (mounted below the plurality of panels 12), a first segment 20 of a capacitive wire, and a second segment 22 of a capacitive wire. In some embodiments, the first end 14 may be referred to as the "head" of the bed, while the second end 16 may be referred to as the "foot" of the bed. In FIG. 18, adjustable bed 26 is depicted in a raised position with the first end 14 raised and the second end 16 raised, to reveal a portion of the metal, adjustable bed frame 114 of the adjustable bed 26. In embodiments, the bed frame 114 is a conductive material used to carry a charge and monitor a change in capacitance, as discussed above. Accordingly, in an example where the first end 14 of the adjustable bed 26 is being lowered, detection of human contact with the bed frame 114 may trigger the bed to discontinue downward motion. In some embodiments, detection of contact with bed frame 114 may also trigger a retracting and/or raising of the first end 14. Similarly, in another embodiment, the lowering of second end 16 may be stopped based on detection of human presence by bed frame 114.

Figure 19:
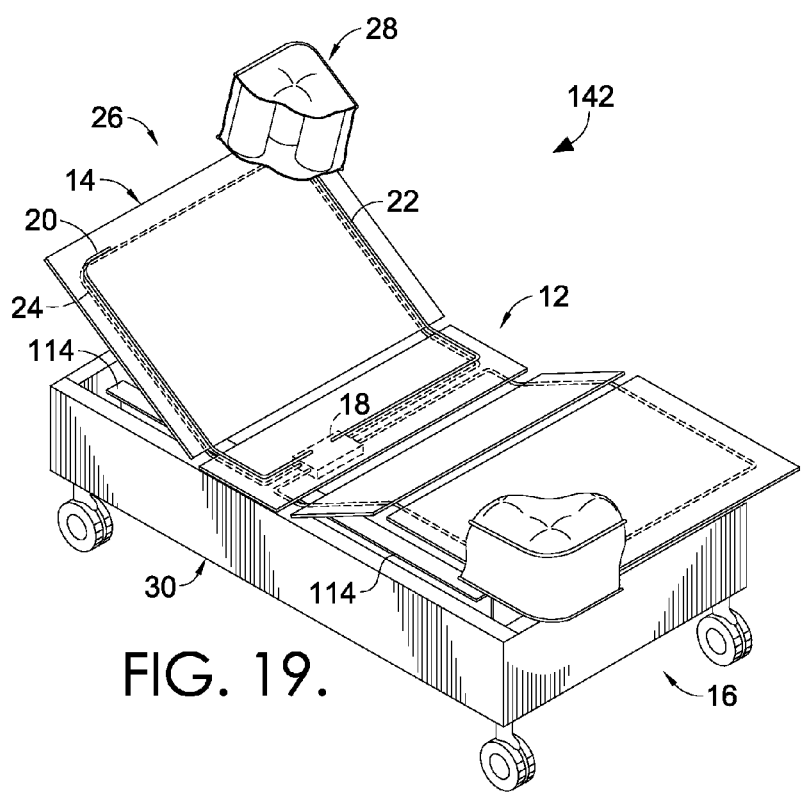
FIG. 19 is a perspective view of the automated bed of FIG. 18, with head and feet portions of the bed raised to partially reveal a metal, adjustable bed frame, and with the mattress cut away to reveal a capacitive wire coupled to the top of the platform and hidden lines indicating the capacitive wire and control enclosure coupled to the bottom of the platform, in accordance with embodiments of the invention.
Figure 20:
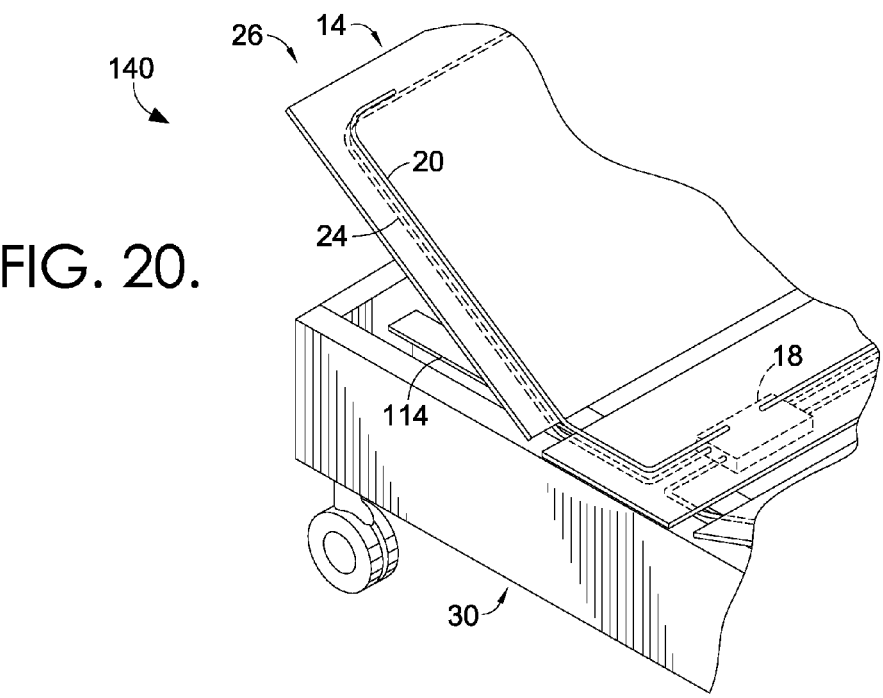
FIG. 20 is an enlarged, perspective view of the automated bed of FIG. 19, with head and feet portions of the bed raised to partially reveal a metal, adjustable bed frame, and with a capacitive wire coupled to the top of the platform and hidden lines indicating the capacitive wire and control enclosure coupled to the bottom of the platform, in accordance with embodiments of the invention.

As can be seen in FIG. 18, capacitive wiring around a perimeter of a platform may be used in addition or alternative to the capacitive detection using bed frame 114. Accordingly, FIG. 19 depicts the adjustable bed of FIG. 18 with a majority of the mattress 28 removed. As can be seen on the plurality of panels 12, first and second segments 20 and 22 of capacitive wire detect presence above the platform (e.g., on top of the mattress), while the third segment 24 detects presence below the platform (e.g., under the bed). An enlarged view of FIG. 19 is shown in FIG. 20, with hidden lines depicting capacitive wires 20 and 24 coupled to the control enclosure 18, which is mounted beneath the panels 12. Further, the metal frame 114 is shown below the mattress 28 and can be used to detect presence, in addition or alternative to the capacitive wire segments on the platform 12.

Figure 21:
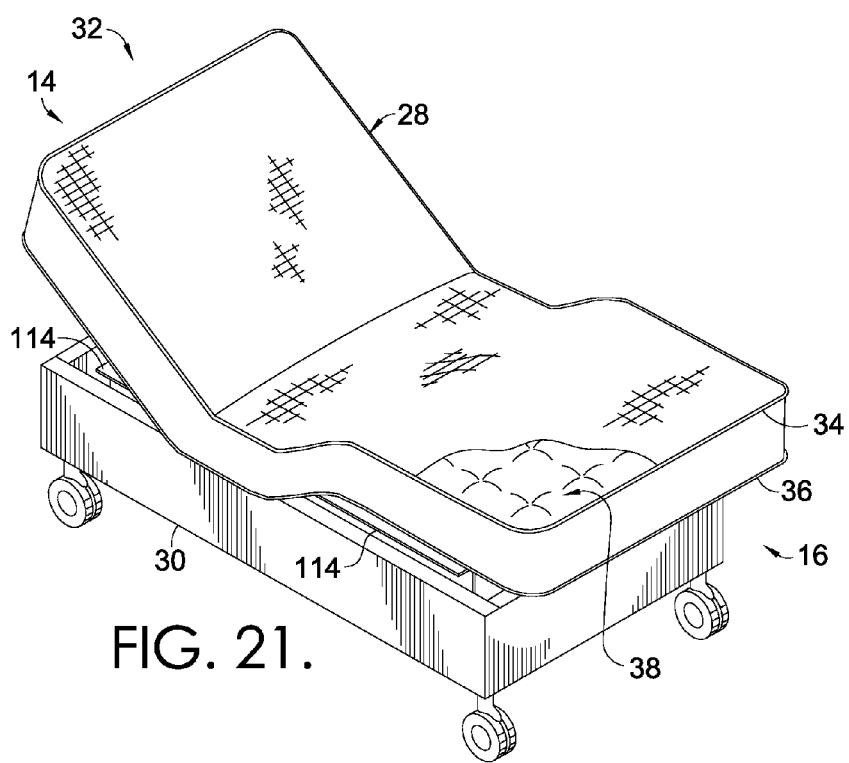
FIG. 21 is a perspective view of an automated bed with head and feet portions of the bed raised to partially reveal a metal, adjustable bed frame, and a tape edge surrounding a perimeter of the mattress cover, in accordance with embodiments of the invention.

With reference to FIG. 21, an enlarged, perspective view of the automated bed of FIG. 19 with head and feet portions of the bed raised to partially reveal a metal, adjustable bed frame 114 is shown. Additionally, in some embodiments, a conductive wire may be incorporated into the top tape edge 34 around the top surface of the mattress 28. In another example, a conductive wire may be incorporated into the bottom tape edge 36 around the bottom surface of the mattress 28. During manufacturing, a conductive wire may be inserted into the tape edge automatically, as the tape edge is applied to a mattress covering. In some embodiments, when routed through the tape edge perimeter, the sensitivity of the conductive wire may be adjusted in software associated with a processor used to determine presence detection. Accordingly, in some embodiments, presence may be detected with respect to an adjustable bed using both wiring incorporated into the perimeter of the mattress and the metal, adjustable bed frame 114 itself being used as a capacitive sensor.

Figure 22:
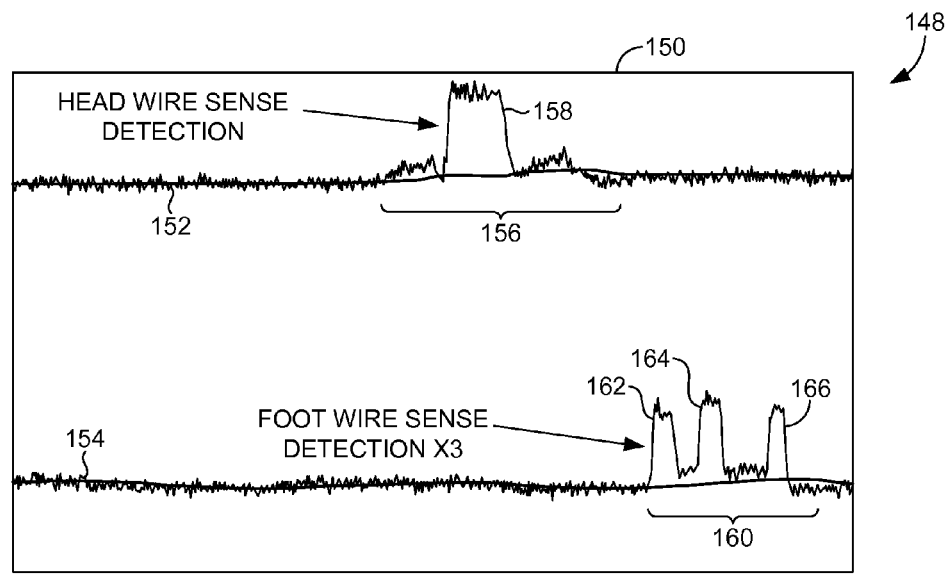
FIG. 22 is an exemplary graphical display of the measure of head wire sense detection and foot wire sense detection associated with an adjustable bed, using capacitance monitoring, in accordance with embodiments of the invention.
Figure 23:
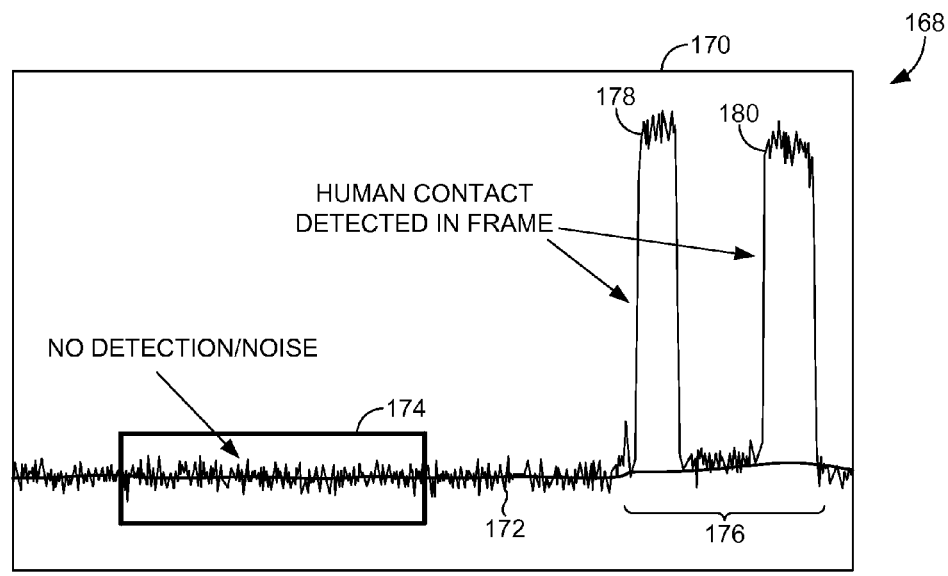
FIG. 23 is an exemplary graphical display of the measure of contact detection with a metal, adjustable bed frame using capacitance monitoring, in accordance with embodiments of the invention.
Figure 24:
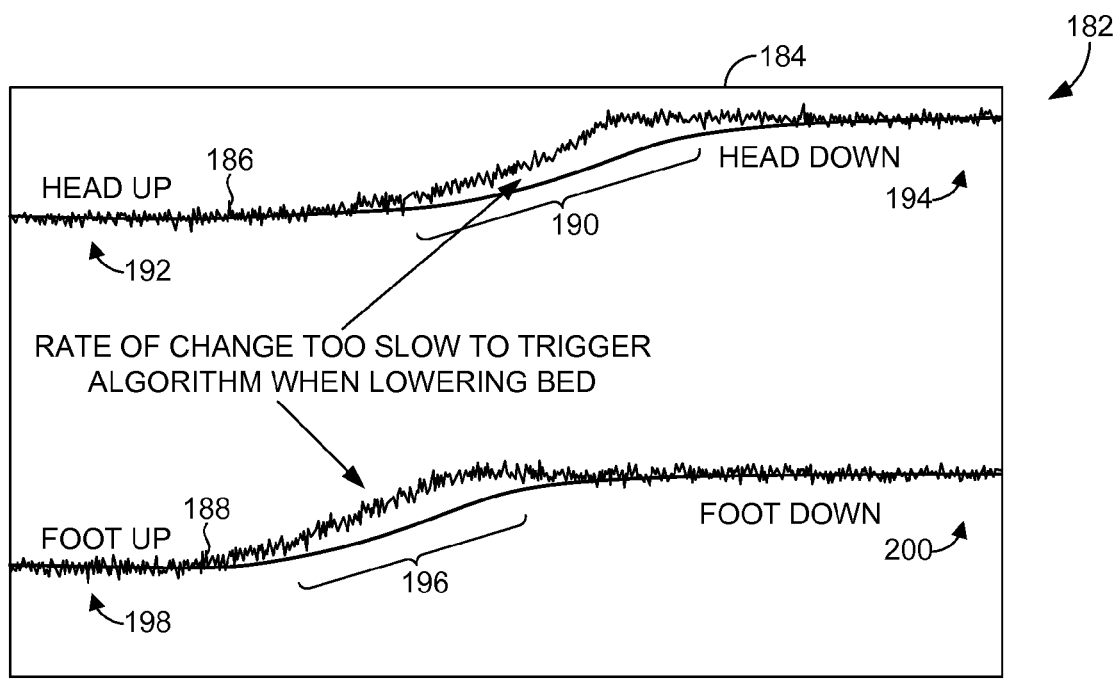
FIG. 24 is an exemplary graphical display of the measure of the rate of change of monitored capacitance during lowering of the head portion and foot portion of a metal, adjustable bed frame, in accordance with embodiments of the invention.

With reference to FIGS. 22-24, capacitive detection is monitored over time, noting changes in capacitance due to presence detection, noise interference, and movement of the automated bed. For example, in FIG. 22, capacitance detection 148 is shown on a display 150 that includes both head wire monitoring 152 and foot wire monitoring 154. As shown along the path of the head wire monitoring 152, head wire sense detection area 156 indicates a peak 158 of change in capacitance. Similarly, along the path of the foot wire sense monitoring 154, foot wire sense detection area 160 indicates three peaks 162, 164, and 166 that indicate changes in capacitance. Accordingly, in one embodiment, a capacitive wire near a first end 14 (head) of an adjustable bed may detect a change in capacitance (such as peak 158) that triggers one or more features of the adjustable bed. In another embodiment, a capacitive wire near a second end 16 (foot) of an adjustable bed may detect a change in capacitance (such as one or more of the peaks 162, 164, and 166) and be used to trigger one or more features of an adjustable bed. In some embodiments, triggering a feature of an adjustable bed requires satisfying a threshold for detection. In other words, the monitoring system may detect changes in capacitance in relation to the head or foot portions of the bed, but the change in capacitance may not be great enough to satisfy a threshold for detection that triggers a feature. For example, minimal movement of a person on a mattress may indicate some level of change in capacitance to the monitoring system without triggering any change in movement of the bed or activity of associated features. Meanwhile, complete removal of a user from a bed, which alters the detected capacitance above a particular threshold, may indeed trigger the threshold for an associated activity, such as lowering the foot of the bed and/or triggering lights to come on.

Turning next to FIG. 23, capacitance detection 168 is shown on a display 170 that includes monitoring of capacitance 172 of a metal, adjustable bed frame. Detection area 174 designates the indication of no presence being detected and also provides an indication of the inherent level of noise that is detected by the system. Further, detection area 176 indicates peaks 178 and 180 of changes in capacitance, which exhibit that human contact with the bed frame has been detected. As discussed above, a threshold for detection may be determined, such that a minimal amount of contact, for a short period of time, may not trigger an indication of presence with respect to the bed frame. At the same time, contact with the bed frame for a longer period of time, as indicated by a large change in capacitance for a longer duration, may be associated with a determination of presence under and/or near the bed frame. In embodiments, detection of human contact with the frame, as indicated by peaks 178 and 180, may trigger a number of features associated with the adjustable bed, such as stopping of a lowering feature, alerting of an alarm feature, retracting of motion in an upward direction for a specified distance, or any combination of features programmed to activate in response to the appropriate trigger.

With reference to FIG. 24, capacitance detection 182 is shown on display 184 to demonstrate the amount of change in capacitance over time with respect to the frame of an adjustable bed, such as the adjustable bed frame monitored in FIG. 23. Display 184 includes the monitoring of a head portion 186 and a foot portion 188 of an adjustable bed. In embodiments, the rate of change area 190 is monitored as the capacitance changes from a first level of capacitance 192 to a second level of capacitance 194. Similarly, rate of change area 196 is monitored as the capacitance changes from a first level of capacitance 198 to a second level of capacitance 200. In embodiments, the rate of change in capacitance impacts whether the change itself triggers any feature of the automated bed. Accordingly, as indicated on the display 184, the rate of change area 190 and the rate of change area 196 indicate to a processor and/or controller that the rate of change in capacitance is occurring over too long of a time (i.e., is too slow) to trigger any of the features of the adjustable bed associated with lowering of the bed. For example, an algorithm that requires a minimum amount of change in capacitance before stopping lowering a bed (i.e., an algorithm that requires detection of the presence of human contact) may not be triggered by the change in capacitance caused by the movement of the bed itself, such as in FIG. 24.

As will be understood, a variety of filtering techniques may be used to adjust the determinations made (regarding whether presence is or is not detected) using software associated with the processor. For example, a variety of filters or transforms may be applied to the monitored capacitance signal to adjust/adapt the software for a particular application or user. For example, an automated bedding system could be adapted to adjust lighting or other functions based on particular amounts of change in capacitance over particular amounts of time, or trigger particular functions during particular times of day/night. As such, a processor may be trained to alter the sensitivity of a threshold based on previous use by a particular user of a corresponding feature. Additionally, a reaction time may be changed and a threshold may be adjusted for different users and different features of the automated bed.

Figure 25:
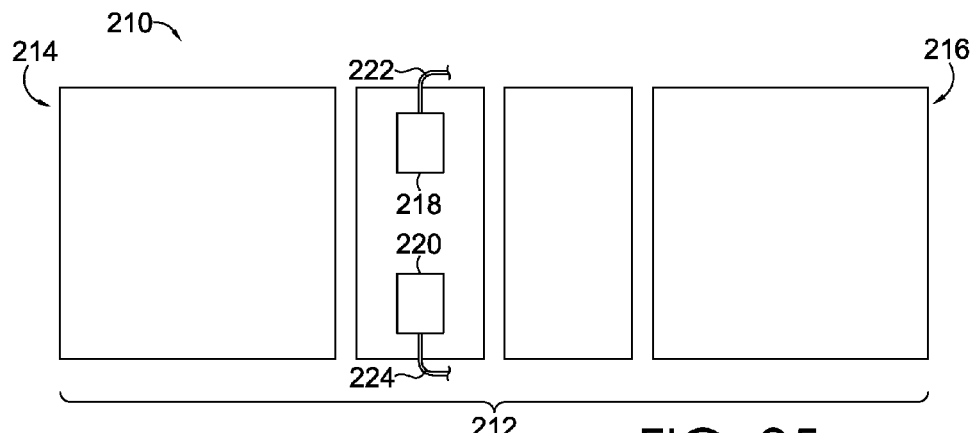
FIG. 25 is a top view of detection pads coupled to the panels of an automated bed platform, in accordance with embodiments of the invention.
Figure 26:
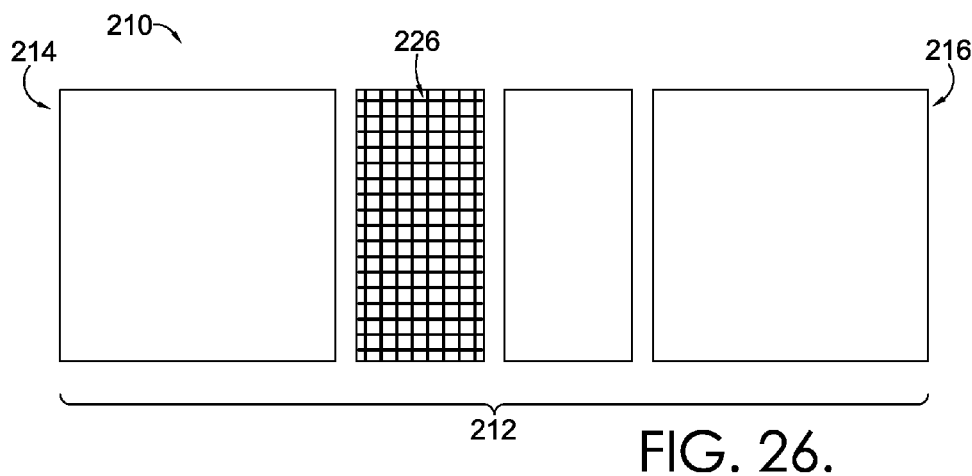
FIG. 26 is a top view of a detection grid coupled to the panels of an automated bed platform, in accordance with embodiments of the invention.
Figure 27:
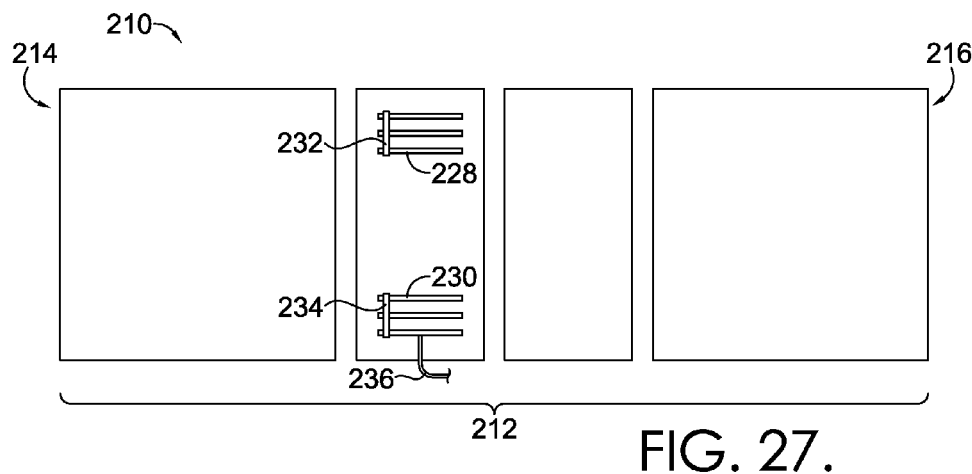
FIG. 27 is a top view of detection strips coupled to the panels of an automated bed platform, in accordance with embodiments of the invention.

An embodiment of an automated bedding system 210 with capacitive wire sensing is seen in FIGS. 25-27. Referring first to FIG. 25, a top view of the platform of the automated bedding system 210 includes a plurality of panels 212 having a first end 214 and a second end 216, detection pads 218 and 220 coupled to a surface of the plurality of panels 212, and cables 222 and 224 coupled to detection pads 218 and 220. In some embodiments, the first end 214 may be referred to as the "head" of the bed, while the second end 216 may be referred to as the "foot" of the bed.

When viewed from the top in FIG. 25, detection pads 218 and 220 are generally arranged near the first end 214 of the automated bedding system 210. In one embodiment, detection pads 218 and 220 are coupled to a stationary panel of the plurality of panels 212, which may be referred to as a "seatboard." As such, while the single panel supporting the head of the bed and the double panels supporting the foot of the bed may articulate up and down, the non-articulating seatboard may remain stationary. In one embodiment, while detection pads 218 and 220 are coupled to a static portion of an automated bedding system 210, an occupancy determination may be made with respect to one or more of the plurality of panels 212.

In some embodiments, detection pads 218 and 220 are a capacitive material, adapted to have a voltage based on proximity of an object to the detection pads 218 and 220. In further embodiments, the detection pads 218 and 220 are an aluminized polymer material with conductive properties. The aluminized polymer material of detection pads 218 and 220 may be conductive on one side only. In one embodiment, detection pads 218 and 220 are Mylar® pads. The capacitance measured across such conductive, aluminized polymer pads may be monitored by a processor that uses software to generate a determination of occupancy detection. In further embodiments, detection pads 218 and 220 may be aluminized Mylar®, aluminum sheets, metal screening, aluminum tape, a wire grid for a seat board, a metalized material or fabric, or any aluminized polymer material with conductive properties. In some embodiments, upon detection of occupancy, the system activates one or more features and/or accessories via a control box and a signal acting as a switch, using technologies such as Bluetooth, Wi-Fi, and Zigbee. In some embodiments, detection pads 218 and 220 have a single side that is conductive and may be coupled to a bottom surface of an automated bedding system 210 platform, such as being sandwiched between stationary parts of an automated bedding system 210 during assembly.

In one embodiment, a Microchip® brand capacitive sensor may be used to determine when occupancy is detected. As such, while occupancy detection relies on the juxtaposition of a person or body with respect to one or both of the detection pads 218 and 220, a determination of the level of detection or the measurement of occupancy is conducted digitally, in software associated with the processor. In some embodiments, software associated with the occupancy detection system includes a software protocol that provides for seamless control of remote accessories associated with an automated bedding system.

As shown in FIG. 25, the capacitive detection pads 218 and 220 may be coupled to a control enclosure 218 coupled to the plurality of panels 212 of the automated bedding system 210. In some embodiments, cables 222 and 224 are coupled to the detection pads 218 and 220 and to a controlling device, such as a control enclosure/box. In embodiments, cables 222 and 224 are coaxial cables. As will be understood, additional capacitive components, such as additional detection pads, may be coupled to the plurality of panels 212. For example, while detection pads 218 and 220 may be coupled to a top surface of the plurality of panels 212, additional detection pads may be coupled to the bottom surface of the plurality of panels 212. Further, although depicted on a top surface of the plurality of panels 212, in some embodiments, detection pads 218 and 220 are coupled to any surface of the automated bedding system 210. For example, detection pads 218 and 220 may be coupled to a bottom surface of the plurality of panels 212 during assembly of an automated bedding system 210.

Detection pads 218 and 220 may be used to detect occupancy with respect to an automated bedding system 210. For example, as arranged near first end 214 of the automated bedding system 210, the torso of a person positioned on the top of the automated bedding system 210 may be detected by detection pads 218 and 220. In embodiments, detection pads 218 and 220 create a defined sensing area on the top half of the head of the bedding system 210 and are less susceptible to noise interference from articulation of the rest of the automated bedding system 210.

Referring next to FIG. 26, a top view of the platform of the automated bedding system 210 includes the plurality of panels 212 having a first end 214 and a second end 216, and a wire grid 226. Wire grid 226 may be coupled to a control enclosure/box for controlling the automated bedding system 210. In further embodiments, the wire grid 226 may be coupled to a controller that is external to the bedding system 210.

In some embodiments, wire grid 226 provides similar occupancy detection functionalities as the detection pads 218 and 220. Additionally, although depicted in FIG. 26 as being coupled to a particular portion of a top surface of the plurality of panels 212, in some embodiments, wire grid 226 may be coupled to any portion of the automated bedding system 210 for related detection purposes. In the embodiment of FIG. 26, wire grid 226 is made from a metallic detection material, such as an aluminized material or fabric, aluminized wire, or other metallic screen material. In one embodiment, the metallic screen material of wire grid 226 is interwoven to form a detection pad, such as detection pad 218 and 220 of FIG. 25.

Turning now to FIG. 27, a top view of the platform of the automated bedding system 210 includes a plurality of panels 212 having a first end 214 and a second end 216, a series of detection strips 228 and 230 coupled to the plurality of panels 212. The series of detection strips 228 and 230 are interconnected using connecting strips 232 and 234. In further embodiments, one or both of the series of detection strips 228 and 230 may be coupled to a control enclosure/box for controlling the automated bedding system 210, such as coupling detection strips 230 to a control enclosure using a cable 236. For example, cable 236 may be a coaxial cable coupling the series of detection strips 230 to a controller of the automated bedding system 210.

In some embodiments, a detection material associated with the automated bedding system 210 may be coupled to a top side of a plurality of panels 212 and/or a bottom side of the plurality of panels 212, and may be coupled directly to the deck of the automated bedding system 210 (i.e., to at least a portion of the plurality of panels 212). The detection materials depicted in FIGS. 25-27 as being coupled to the plurality of panels 212 may be arranged in any configuration for detection of occupancy. In some embodiments, non-conductive components of the automated bedding system 210 are in contact with one or more of the sensors (i.e., detection strips 228 and 230, detection pads 218 and 220, and/or wire grid 226). In one example, a non-conductive control box may be coupled to one or more capacitive sensors.

Figure 28:
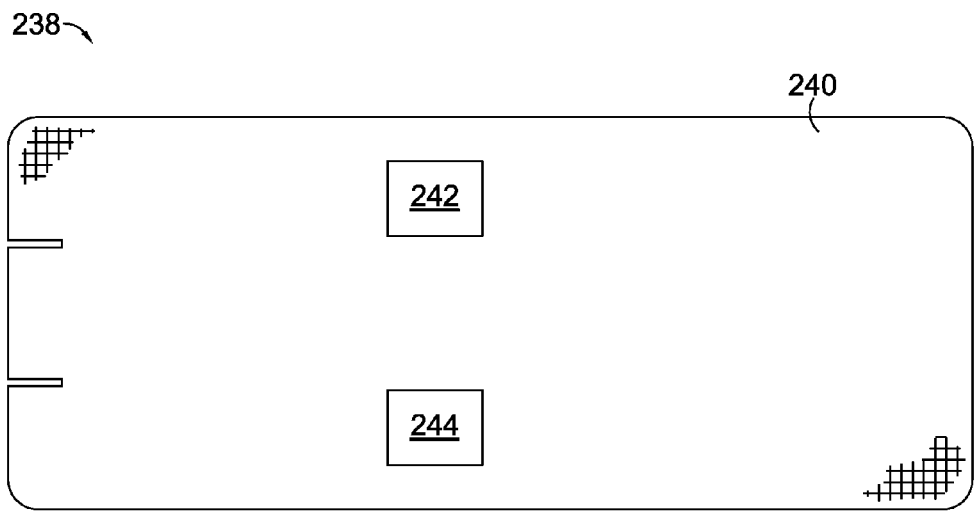
FIG. 28 is a top view of detection pads coupled to a mattress topper material, in accordance with embodiments of the invention.
Figure 29:
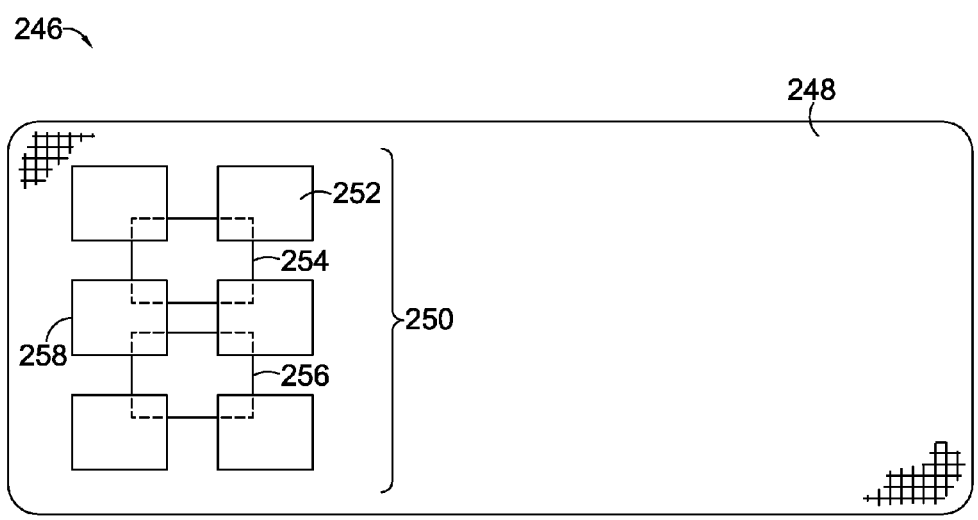
FIG. 29 is a top view of an array of detection pads coupled to a mattress topper material, in accordance with embodiments of the invention.

With reference now to FIGS. 28 and 29, embodiments of an occupancy detection system include incorporating a detection material, such as one or more detection pads, into a mattress topper material of an automated mattress. In the example of FIG. 28, an automated bedding system 238 includes a mattress topper 240 having detection pads 242 and 244 incorporated into the material of the mattress topper 240. In one embodiment, the detection pads 242 and 244 are aluminized sections applied to the topper material of mattress topper 240. In further embodiments, mattress topper 240 is fused with a metallic material, and detection pads 242 and 244 are pre-applied, metalized areas on the surface of mattress topper 240.

As shown in the automated bedding system 246 of FIG. 29, and array 250 of multiple detection pads 252 may be coupled to a surface of a mattress topper 248. In embodiments, a detection pad 252 may be an aluminized polymer material pad positioned on the mattress topper 248 with a conductive side facing upward and arranged in a variety of positions. In further embodiments, detection pads 252 may be overlapped, arranged on left and/or right sides of a mattress topper 248, or otherwise configured to provide an area of detection with respect to the automated bedding system 246. In one embodiment, a plurality of detection pads 252 are arranged in an array 250 configuration such that a position of a single occupant of a bed can be located.

For example, detection pads 252 in FIG. 29 may be aluminized polymer material panels placed in an array 250 to determine an occupant's position, by overlapping with detection pads 254 and 256. In one example, a detection pad 258 is coupled to and/or overlaps with both detection pads 254 and 256, and is positioned in the middle of the array 250 to detect occupancy with respect to both sides of a mattress (e.g., a first occupant lying on a left side of a bed and a second occupant lying on a right side of a bed, with the heads of each occupant near the first end 214). In some embodiments, a non-conductive material may be used to arrange the array 250 and can be coupled directly or indirectly to the aluminized polymer material of detection pads 252, 254, 256, and 258.

In one embodiment of the invention, an aluminized polymer detection material may be tied directly to a helical spring of an automated bedding system for detection. For example, a detection material may be coupled to an inner spring unit of an automated bedding system to create a single sensor from the combined detection of each spring in the inner spring unit. In another embodiment, individual pocket coils of a mattress could become individual occupancy detectors as the coils are insulated from one another. As such, the pocket coils could serve as an array of individual sensors. In some embodiments of the invention, capacitive detectors such as aluminized polymer pads may be used with an automated bedding system mattress that includes pocket coils, memory foam, and/or air. For example, two or more aluminized polymer material sensors may be coupled to a platform of an automated bedding system to generate at least two distinct zones of detection with respect to be bed. In some embodiments, aluminized polymer material sensors and/or pocket coils could be used to identify multiple, individual areas and/or zones on a bed for detection of occupancy.

Various embodiments of the invention utilize the occupancy detection systems of FIGS. 25-29 for determining occupancy of an automated bedding system, and for triggering and/or activating one or more controls and/or features associated with the automated bedding system. For example, one or more Mylar® detection pads may be used to determine when an occupant exits a bed, which may trigger one or more commands associated with the bed, such as turning on a light on that occupant's side of the bed. As such, the under-bed lighting on a first user's side of a bed may be illuminated based on detection of that first user exiting the bed.

The features triggered by changes in occupancy detection may be dependent on the time of day during of the occupancy determination. For example, upon determining a change in occupancy at a particular time of night (i.e., a determination that a user has exited a bed in the middle of the night) may trigger the turning on of lights associated with a bathroom, such as a light in the bathroom and/or a series of lights along a path to the bathroom. In further embodiments, a change in occupancy detection may trigger one or more features associated with a remote controller of an automated bed. For example, an occupancy change may trigger an alarm to chime, which could turn on one or more lights in response to triggering the remote. In further embodiments, features that are activated/triggered by a change in occupancy detection (such as a detection panel sensing the absence of a person) could be deactivated and/or timed out after a particular amount of time. In another embodiment, a snooze feature may be incorporated into the detection system such that an occupancy detection that triggers a particular feature of the automated bedding system may be postponed and/or delayed.

In one embodiment of the invention, the occupancy detection system may be provided for use with a non-adjustable bed, such as a child's bed. As such, a detection pad, detection grid, and/or detection strip feature discussed in FIGS. 25-29 may be incorporated into a non-adjustable bed. In one embodiment, the occupancy detection system may be provided as a kit for incorporating into an existing, non-adjustable bed. The system may be used to detect occupancy with respect to the non-adjustable bed, such as alarming if a child gets out of bed, by chiming a bed remote and/or causing a light to come on in a room. In one embodiment of the invention, depending on a time of night when the change in occupancy detection is sensed, one or more features of the bed system may be triggered, such as turning on lights to a child's bathroom, etc.

In embodiments of the invention, occupancy detection triggers both activation and deactivation of features associated with a bed. For example, an occupancy detection system may determine that a person has entered a bed, which may trigger the system to turn off the lights in the room. Accordingly, in one embodiment, a first change in occupancy determination (a user exiting a bed) may trigger lights to be turned on in a room, while a second change in occupancy determination (a user returning to bed) may trigger the lights to turn back off. In some embodiments, lights may be dimmed upon sensing a user getting into bed, timed to turn off after a particular amount of time passes after occupancy is detected, and/or dimmed to dark upon occupancy detection. For example, lights may be dimmed to dark upon detection of an occupant returning to bed.

Further embodiments of the invention include coordinating of additional features associated with the occupancy detection system, such as a home alarm system that may be set and/or turned on based on detecting that a person has gotten into bed. In further embodiments, the home alarm system may be deactivated upon the person exiting the bed. In yet another example, exterior lights of a house may be turned on based on detecting a user exiting the bed, such as a front porch light turning on when a user exits the bed in the middle of the night.

In one embodiment, the occupancy detection system may be used in a home care situation for an elderly or disabled individual. Accordingly, the system may be programmed to trigger certain alarms when the elderly or disabled person gets out of bed, such as by chiming a remote and/or alarm feature of the occupancy detection system. In another embodiment, various features of a user's home may be coordinated to operate in response to determinations by the occupancy detection system. For example, if the occupancy detection system determines that a user is in bed, the home environment system (i.e., the Heating, Ventilation and Air Conditioning (HVAC) system) may be adjusted to a user-specified night setting. Similarly, if the occupancy detection system determines that a user has exited a bed, such as determining that a detection pad no longer senses the presence of the occupant, then the HVAC system may be triggered to change to daytime settings.

In some embodiments of the invention, the occupancy detection system may be incorporated into a variety of other household devices, other than a bed or bedding system. For example, an occupancy detection system may be incorporated into a door mat, an area rug, and/or a stairway of a home for indication of occupancy presence. For example, in one embodiment, the occupancy detection system may be incorporated into a runner on a basement stairway. Based on a determination of occupancy, the system may trigger an audible alarm to alert that presence is detected, such as alerting a warning signal when a child's presence is detected near basement stairs.

Figure 30:
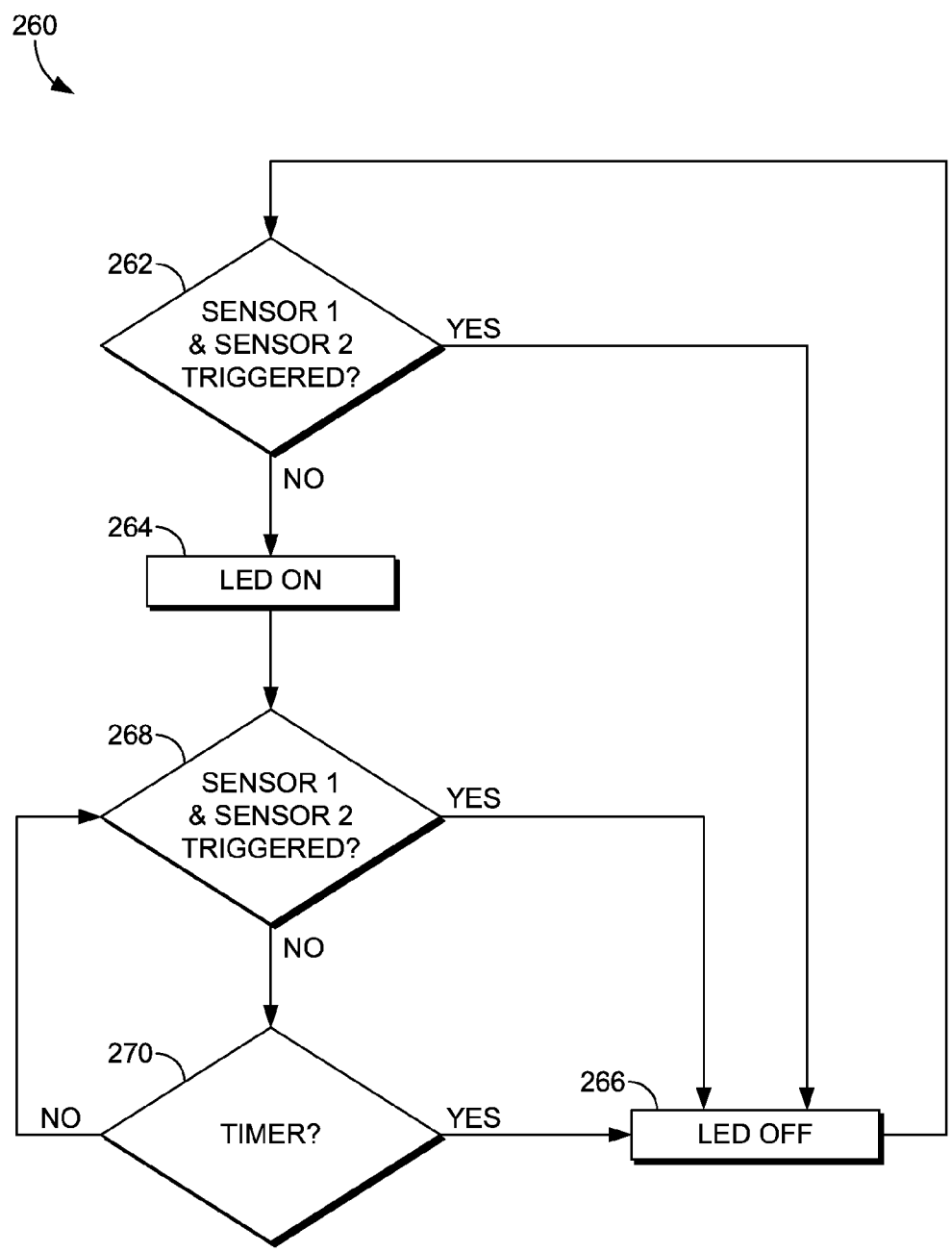
FIG. 30 is a flow diagram of an exemplary method of detecting occupancy with respect to a bed, in accordance with embodiments of the invention.

Having described various embodiments of detection using the occupancy detection system, exemplary methods for implementing the occupancy detection system are discussed with reference to FIGS. 30-32. In particular, FIG. 30 is flow diagram 260 of an exemplary dual-sensor method of detecting dual occupancy with respect to an adjustable bed. At block 262, a determination is made whether a first sensor and a second sensor have been triggered. For example, software executed by the system may determine whether both occupants of a bed are present, having a sensor associated with a potential position of each occupant. If both of the sensors have not been triggered, at block 264, an LED may remain on. For example, if both occupants have not gotten into bed yet, LED under-bed lighting may remain lit. Alternatively, if sensor 1 and sensor 2 have been triggered, at block 266, an LED may be turned off. For example, in FIG. 25, if detection pads 218 and 220 are both triggered to indicate presence of two individuals in the automated bedding system 210, then a determination may be made to turn off the lights in a room, such as an under-bed lighting feature of a bed.

At block 268, the occupancy detection system continues to check whether the first and second sensors have been triggered. If the sensors have not been triggered, at block 270, a timer may be initiated to turn off the light at block 266 after a specified interval of time has passed. In other words, the system will not wait all night for both occupants to get into bed before turning off the lights. Alternatively, if a timer is not initiated, the method returns to block 268 where the system continues to check for a triggering of the first and second sensors before turning off the LED. In one embodiment, a user may indicate to a bed system that only one occupant is present, which may permit the system to only require detection from a single sensor before turning off the lights.

Figure 31:
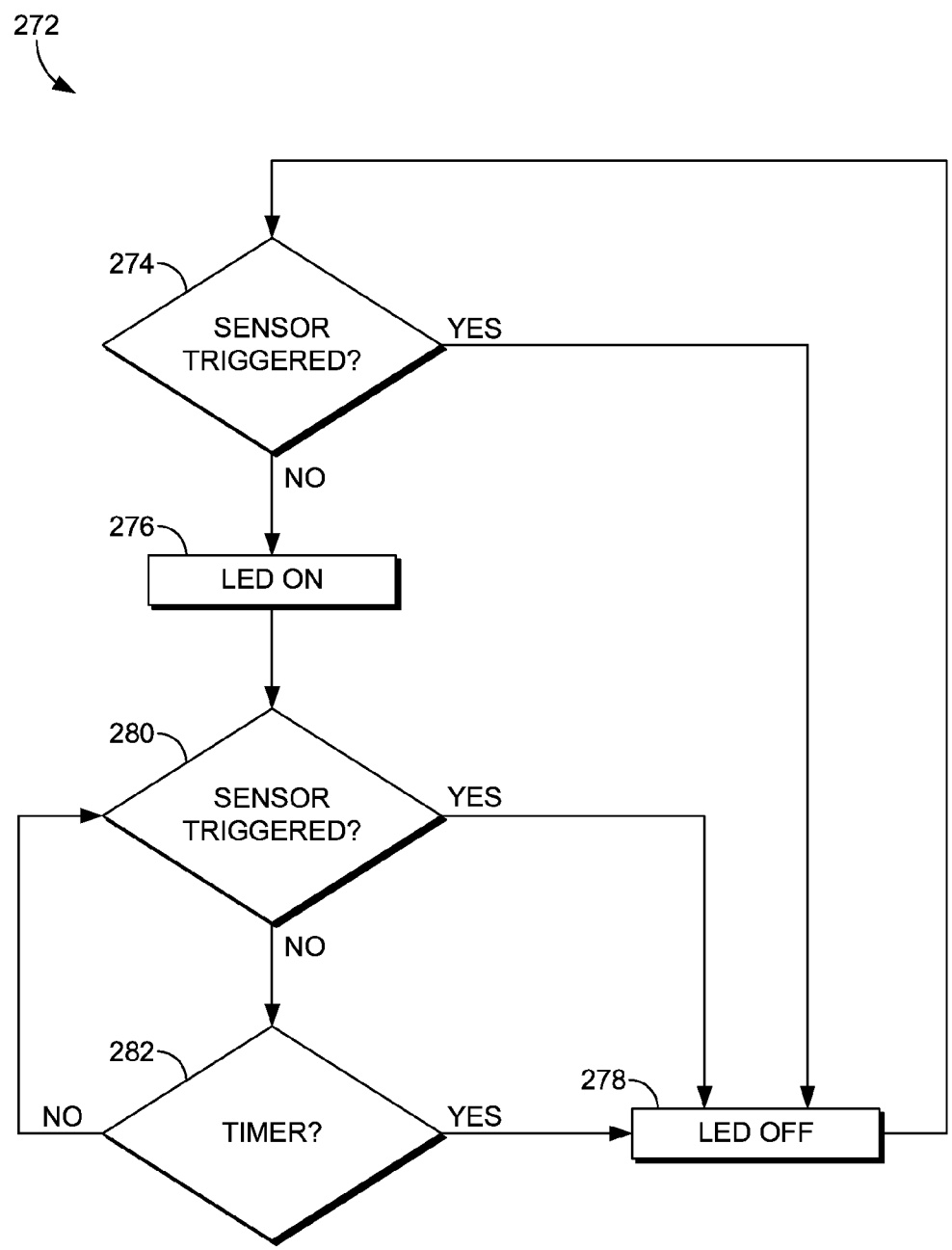
FIG. 31 is a flow diagram of an exemplary method of detecting occupancy with respect to a bed, in accordance with embodiments of the invention.

Turning now to FIG. 31, a flow diagram 272 of an exemplary single-sensor method of detecting occupancy with respect to a bed is provided. At block 274, a determination is made whether a sensor has been triggered. At block 276, if the sensor has not been triggered, the LED remains on. For example, if a sensor of an automated bed has not determined that an occupant has entered the bed, then under-bed, LED lighting may remain on to illuminate a path to the bed. However, if the sensor is triggered at block 274, then the LED is turned off at block 278 (e.g., the occupant gets into bed and triggers the sensor). Having left the LED on at block 276, a determination is made at block 280 as to whether the sensor is subsequently triggered. If the sensor has been triggered, the LED is turned off at block 278. If the sensor has not been triggered, at block 282, a timer may be initiated to determine when a threshold amount of time has passed. After an amount of time has passed, the timer may trigger the LED to turn off at block 278. Alternatively, upon not satisfying the threshold of time by the timer at block 282, the method may return to block 280 to make a determination of whether the sensor has been triggered.

Figure 32:
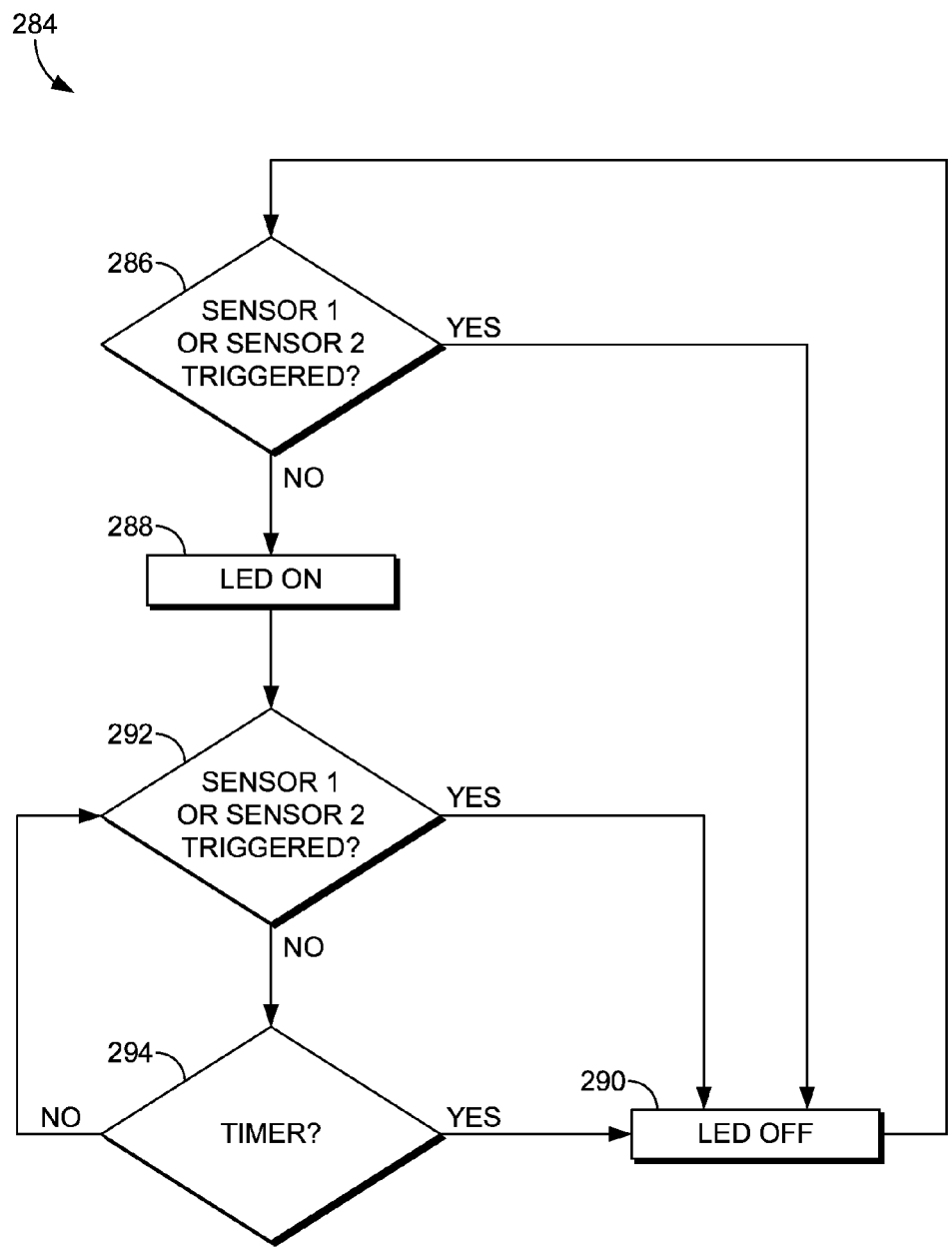
FIG. 32 is a flow diagram of an exemplary method of detecting occupancy with respect to a bed, in accordance with embodiments of the invention.

With reference finally to FIG. 32, a flow diagram 284 of an exemplary dual-sensor method of detecting single occupancy with respect to a bed is provided. At block 286, a determination is made whether a first sensor or a second sensor has been triggered. For example, a bed may have two (or more) sensors that define at least two distinct areas of the bed for detection. If neither of the sensors has been triggered, at block 288, an LED may remain on. Alternatively, if sensor 1 or sensor 2 has been triggered, at block 290, an LED may be turned off. For example, if one of two sensors is triggered, under-bed LED lights may be turned off. In another example, as depicted in FIG. 25, if detection pad 218 or detection pad 220 is triggered to indicate presence of a body in the automated bedding system 210, then a determination may be made to turn off the lights in a room.

At block 292, the occupancy detection system continues to check whether the first or second sensor has been triggered. If neither sensor has been triggered, at block 294, a timer may be initiated to turn off the light at block 290 after a specified interval of time has passed. Alternatively, if a timer is not initiated, the method returns to block 292 where the system continues to check for a triggering of the first and second sensors before turning off the LED.

As will be understood, although the examples of FIGS. 30-32 refer to triggering of sensors corresponding to turning an LED light on and off, various embodiments of the invention may trigger additional and/or alternative features associated with an automated bedding system. In other words, although examples of triggering lighting are discussed (in particular, under-bed mounted LED lighting), other features such as a bathroom light, a bedroom fan, house lights, etc., may be triggered by an occupancy determination with respect to a bed. Additionally, the software associated with embodiments of the system may be customized to a particular system in that both single-occupant and dual-occupant features may be adjusted to respond differently to various triggering events.

Accordingly, in a single-occupant embodiment, under-mount LED lighting on an adjustable bed may remain on if the user/occupant is not present and may be turned off once the occupant is detected. In one embodiment of a dual-occupant detection system, the software associated with the sensors may be programmed such that the presence of both users is required before a feature is activated/altered (e.g., both occupants must be present in the bed before the lights will turn off). In another embodiment of a dual-occupant detection system, the system may require that at least one user is present before the lights can be turned off. Further, once the first occupant is present, the system may automatically trigger a timer for turning off the lights without requiring the second occupant to be present in the bed (i.e., a first occupant need not sleep with the lights on all night). However, if the second occupant enters the bed before the timer is complete, the triggering of the second sensor may initiate turning off the lights (without requiring the system to fulfill the entire timer waiting period).

In one embodiment of the invention, a single-occupant system may utilize two sensors for detecting occupancy in an automated bed. The first sensor may make a determination of presence of an occupant in the bed, thereby triggering the turning off of bed lighting (or other associated bed features) without requiring the second sensor to be triggered. As the occupant sleeps, the occupant may shift away from an area of capacitance associated with the first sensor, no longer triggering the first sensor. For example, the occupant may roll from one side of the bed to another. In embodiments, the software of the system may be programmed to allow an amount of delay (i.e., to wait a threshold amount of time) after the first sensor no longer senses an occupant before triggering an associated feature (e.g., before turning on lights because an occupant has left one side of the bed). If the second sensor detects the occupant within the delay period of time (i.e., before the threshold amount of time expires), then the bed may continue to function as if an occupant's presence has been maintained. In other words, if the first sensor no longer senses the occupant but the second sensor detects the occupant within a specified amount of time, the lights need not be turned on because the occupant has just moved from one side of the bed to the other.

In one embodiment, a dual-occupant system may be programmed to permit certain features to be triggered that would otherwise inactivate with a single-sensory system. For example, in an automated bed system with two sensors, a first occupant may trigger a first sensor and a second occupant may trigger a second sensor. With both sensors triggered, the system may be programmed to turn off the lights associated with the bed (e.g., the under-bed LED lighting). If the first occupant exits the bed, under-bed lighting may be activated. For example, one occupant may exit the bed to use the restroom in the middle of the night, and lighting may be illuminated even though the second occupant is still present in the bed. In some embodiments, features such as underbed lighting may be occupant specific, such as under-bed lighting only illuminating on the side of the bed associated with the first occupant and/or first sensor.

In some embodiments, under-bed lighting features associated with an automated bedding system may include photocell light technology. Accordingly, the underbed lighting may not illuminate until night. As such, in some embodiments, the lights will remain on as long as the room is dark (i.e., it is night) and no occupant is present in the bed (i.e., occupant detection is not sensed according to embodiments of the invention).

In embodiments of the invention, the detection material of the detection pads, wire grid, and/or detection strips and the metalized areas of the mattress topper material are adapted to have a voltage based on proximity of an object to the detection material or metalized area. Such voltage information is collected via the detection material and received by a processor, which determines when a change in voltage satisfies a threshold. Once a particular change in capacitance satisfies a threshold, a corresponding function associated with the automated bed may be initiated. In embodiments, a threshold for initiating a corresponding function includes a particular amount of change in voltage within a particular amount of time. For example, when using capacitance information to turn lights on/off, a particular amount of change in voltage may be required during a particular amount of time before satisfying the threshold indicating that a person has exited the bed (and before the lights may be turned on). Similarly, a particular threshold value of voltage change may be required by the processor, over a particular amount of time, before making a determination that a person has re-entered the bed (and before the lights can be turned off again). In embodiments, a processor continuously receives capacitance monitoring information, monitors how quickly a change in capacitance occurs (how quickly the delta changes) to determine if a big enough change has occurred in a certain amount of time to satisfy a threshold, and triggers the corresponding function. Accordingly, based on satisfying a particular threshold, various features associated with the automated bedding system may be activated and/or enabled.

Figure 33:
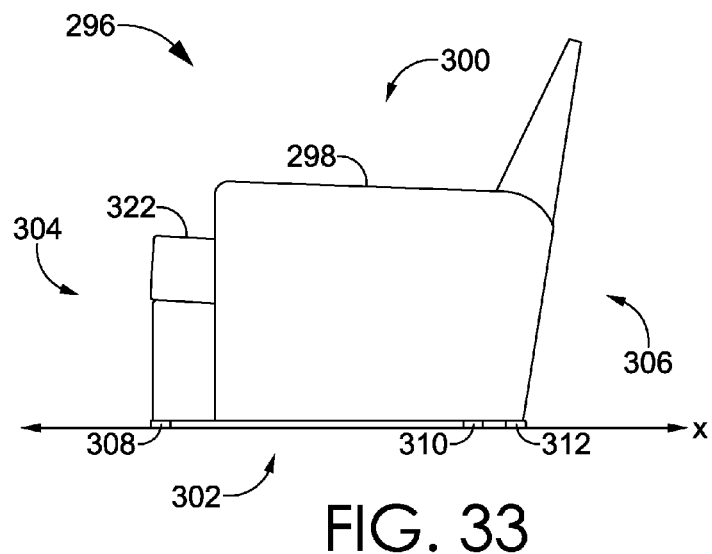
FIG. 33 is a side view of an automated recliner, in accordance with embodiments of the invention.

Turning next to the recliner embodiments of FIGS. 33-38, capacitance detection may be utilized in various automated features associated with a furniture item having a seat, such as an automated recliner and/or lift chair. The exemplary recliner 296 of FIG. 33 is shown from a side view in a lowered position, having a recliner body 298 with a top side 300, a bottom side 302, a front side 304, a back side 306, and a seat top surface 322, and is supported by non-conductive coasters 308, 310, and 312 that insulate the conductive features of the recliner 296 from the ground surface x. As shown in the side view of FIG. 34 in a raised position, the recliner 296 may include one or more conductive features that carry a charge and/or may be monitored for a change in capacitance based on a charge applied to the one or more conductive features. For example, in the embodiment of FIG. 34, the recliner 296 includes a base 314 coupled to conductive support features such as one or more ottoman and/or chair linkages 316 and one or more linear actuators 318. In one aspect, the conductive support features supporting the recliner 296 may include any type of support feature (e.g., metal frame components) utilized by an automated recliner mechanism, such as the conductive features of ottoman and/or chair linkages 316 that are configured to carry a charge applied to the frame of the recliner 296, which may be carried throughout the various linkages 316 underlying the recliner 296 for capacitive detection, as further discussed below.

Figure 34:
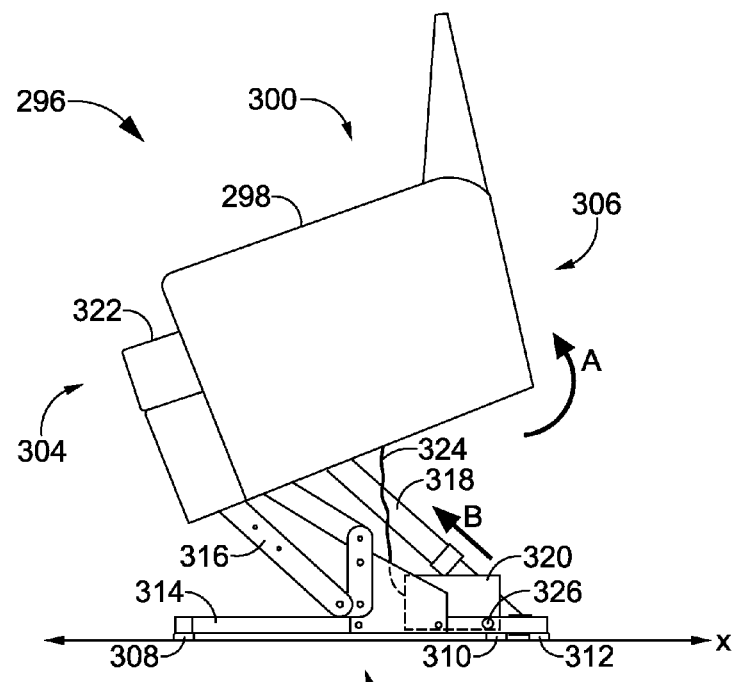
FIG. 34 is a side view of the automated recliner of FIG. 33 in a raised position, in accordance with embodiments of the invention.

The recliner 298 in FIG. 34 is shown in a raised position based on rotation and/or shifting of the chair in an upward direction A, rotating the back side 306 away from the bottom side 302 while tilting the overall recliner body 298 upwards and away from the ground surface x. In some aspects of the invention, one or more linear actuators 318 may be used to shift the recliner 296 into a raised position based on travel in a diagonal, forward direction B relative to the ground surface x. As shown in FIG. 34, the automated features of the recliner 296 may be controlled using a control component 320. The control component 320 may be coupled directly to the support features of the recliner 296, such as coupling directly to the base 314 with conductive connection 326. In further embodiments, the control component 320 may be coupled directly to the base 314 to provide a conductive path across each component of the recliner 296 configured to carry such charge. For example, the control component 320 may be coupled directly to the base 314, which is coupled to multiple linkages 316 that carry a charge, such that a change in capacitance associated with one of multiple conductive features of the coupled base 314 and/or linkages 316 may be detected by a single control component 320. As such, control component 320, linkages 316, and/or linear actuator 318 may act as a sensor for detecting presence with respect to the recliner 296, such as detecting presence of a person in contact with one or more of the conductive features on the bottom side 302 of the recliner body 298.

Figure 35:
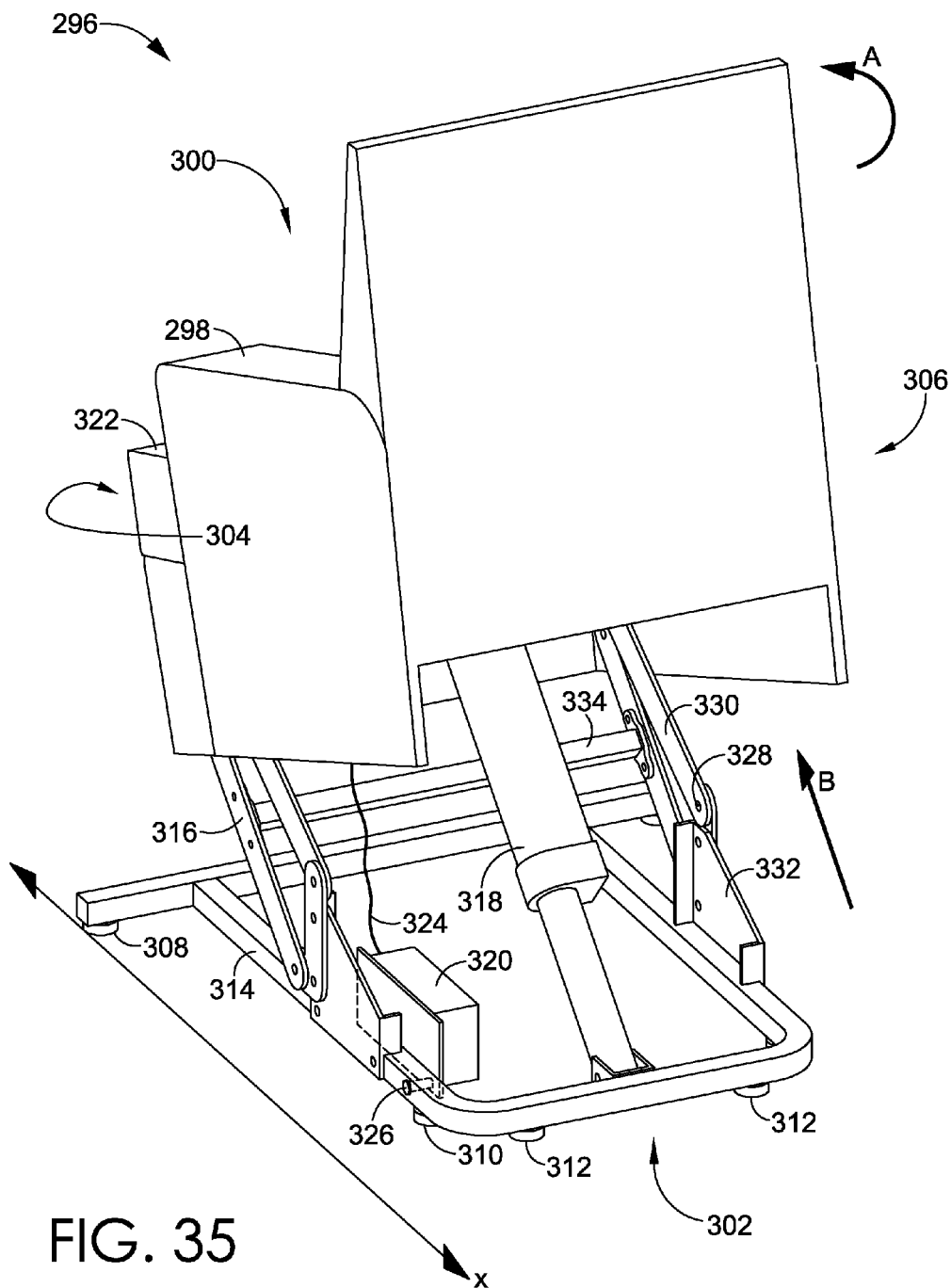
FIG. 35 is a rear perspective view of the automated recliner of FIG. 34, in accordance with embodiments of the invention.

In further embodiments of the invention, FIG. 35 depicts a rear perspective view of an automated recliner 296. The recliner 296 may include conductive features that are coupled to provide a capacitive sensor associated with the control component 320, which may include the base 314, one or more cross-bars 334, one or more linkages 316 and 330, one or more brackets 332, and/or additional conductive features that are configured to carry a charge to provide at least one feature of the capacitive sensor. As such, the combined conductive features on the bottom side 302 of the recliner 296 may collectively provide a capacitive sensor for presence sending with respect to the recliner body 298 based on coupling to the control component 320. For example, with a metal base 314, metal linkages 316, metal cross-bars 334, and/or metal linear actuators 318, the control component 320 may serve as a sensor associated with the automated lift chair recliner 296 to determine whether presence is detected (i.e., via capacitive detection) underneath the chair body 298. While translating in the forward direction B, the recliner body 298 of the automated lift chair 296 may shift into a position where one or more conductive portions of the recliner 296 are exposed on the bottom side 302 and/or back side 306, which provides access to the capacitive sensor coupled to control component 320 (e.g., the capacitive detection sensor comprised of the base 314, the linkages 316 and 330, the actuator 318, the brackets 332, and the cross-bar 334).

In some embodiments of the invention, a conductive feature may be used to couple each of the components of the capacitive sensor together. Such conductive feature may include a conductive bolt, a conductive screw, a conductive pin, and/or an additional conductive linkage that is configured to carry a charge. The capacitive sensing monitored by control component 320 may therefore receive signals from each of the conductive features of the recliner 296 coupled to each other (i.e., an uninterrupted circuit) such that contact with one portion of the recliner 296 is detected by the control component 320 without the control component 320 being directly coupled to each of the features. For example, the cross-bar 334 may be detected by the control component 320 coupled to the base 314 based on a charge carried from the cross-bar 334, through the linkage 316, and through the base 314 to the control component 320. In some embodiments of the invention, control component 320 is configured to receive an indication of change in capacitance from one or more conductive features on the bottom side 302 of the recliner 296 based on user contact with at least a portion of the exposed conductive components on the bottom side 302 of the recliner body 298.

Figure 36:
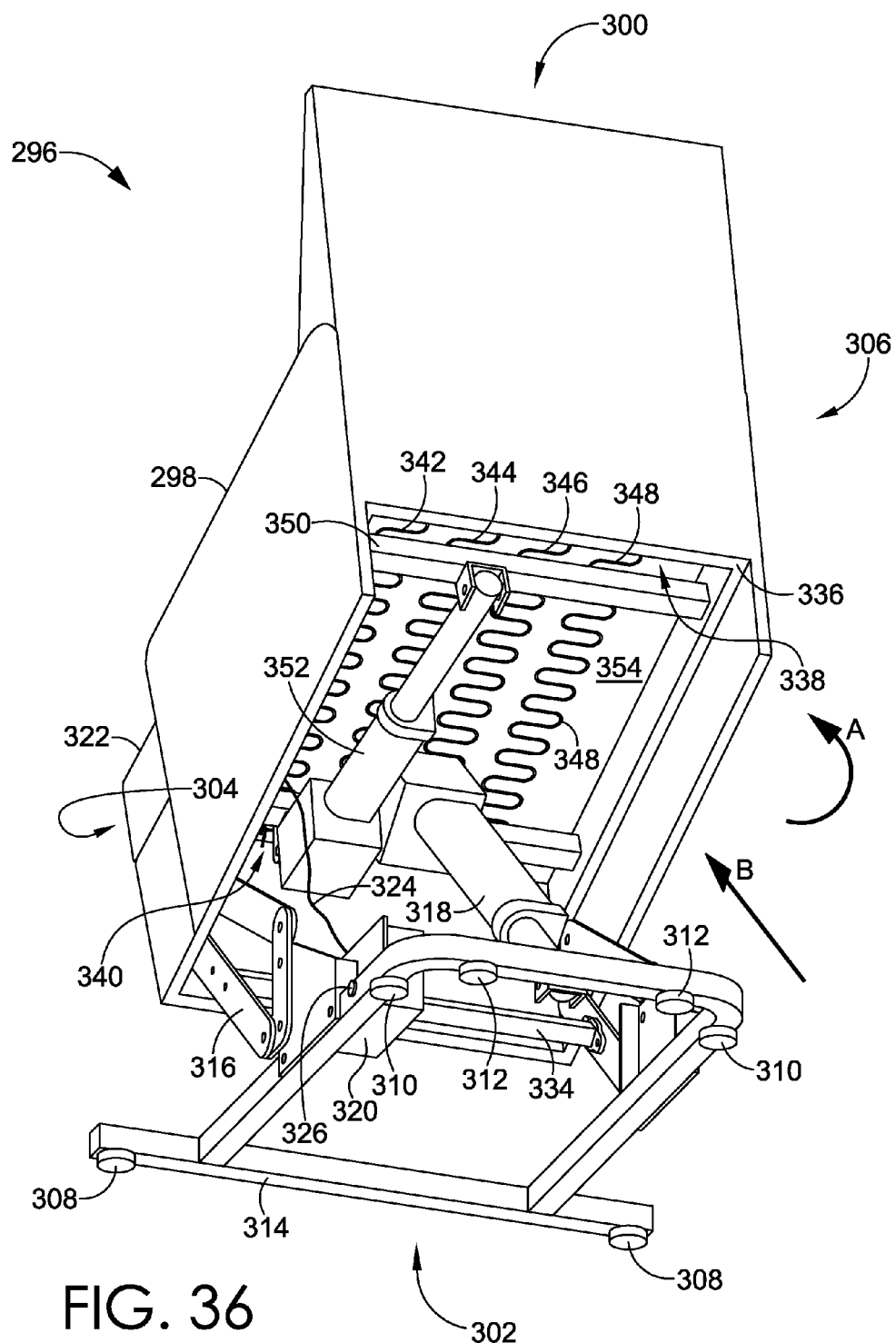
FIG. 36 is a bottom perspective view of the automated recliner of FIG. 34, in accordance with embodiments of the invention.

With reference to FIG. 36, a bottom perspective view of the automated recliner of FIG. 34 depicts further exemplary components that may be coupled into a single circuit for capacitive detection. For example, the cross-bar 350 and the linear actuator 352 may be coupled to the linkages 316 and/or base 314 to provide a capacitive sensor configured to detect presence of a user on the bottom side 302 of the recliner 296. As such, user contact with one or more conductive components on the bottom side 302 may generate an indication to the control component 320 that a user is present underneath the recliner body 298. In one embodiment of the invention, the control component 320 may communicate an indication of presence to activate/inactivate one or more features of the recliner 296. For example, the lift chair mechanisms of the automated recliner 296 may be deactivated (e.g., deactivating one or more linear actuators 352 and 318) during articulation based on an indication of presence. By stopping the travel of one or more features of the automated recliner 296, a person "trapped" beneath the articulating portions of the recliner 296 may be protected from additional injury and/or permitted to move out from underneath the chair while it ceases travel.

By directly coupling the control component 320 to one or more conductive/capacitive features of the recliner 296, such features may serve as a capacitive sensor for presence detection with respect to the chair body 298. In one aspect, the capacitive sensor comprising one or more features on the bottom side of the recliner 296 may interrupt, via control component 320, one or more instances of articulation by the automated features of the recliner 296. For example, an ottoman portion of the chair body 298 may discontinue retracting when presence is detected by one or more linkages 316. In another example, the raising or lowering of the seat top surface 322, based on user command, may be discontinued and/or interrupted once presence is detected by the base 314, linkages 316, cross-bars 334, and the like. As such, capacitive detection of presence with respect to a portion of the chair body 298 may elicit one or more responses from the automated chair to prevent injury to a person in contact with the capacitive sensing features of the recliner 296, regardless of whether a user or other person is directing the recliner 296 to travel in a particular direction (e.g., upward, downward, tilting forward, tilting backward, ottoman extending, ottoman retracting, and/or any other motion that may injure a person contacting the capacitive sensor formed from conductive components coupled to the control component 320).

As further shown in the example of FIG. 36, the recliner 296 may include a seat box 336 having a back end 338 and a front end 340, which is spanned by a set of sinuous wires 342, 344, 346, and 348 that support the seat bottom surface 354. The sinuous wires 342, 344, 346, and 348 are examples of one type/configuration of wire structure for supporting a user seated on the top surface 322 of the recliner 296. In embodiments, the sinuous wires 342, 344, 346, 348, and 350 are coupled to the seat box 336 of the recliner body 298. As shown in the enlarged view of FIG. 37A, such coupling may utilize connection clips 358, 360, 362, and 364 to secure the sinuous wires 342, 344, 346, and 348 to the seat box 336. In embodiments, bridging wire 324 is used to couple the sinuous wires 342, 344, 346, and 348 to form an array at connections 366, 368, 370, and 372. Such capacitive connections via bridging wire 324 may enable each of the sinuous wires 342, 344, 346, and 348 to detect a change in capacitance as an array of sensors coupled to the control component 320 via bridging wire 324.

In FIG. 37A, the sinuous wires 342, 344, 346, and 348 are coupled to the bridging wire 324 to form a connection to control component 324, thereby serving as an occupancy detection array for user occupancy detected with respect to the seat bottom surface 354. In another aspect, the sinuous wires 342, 344, 346, and 348 may form a capacitive detection sensor for receiving an indication of occupancy of the recliner 296 based on coupling of each of the sinuous wires 342, 344, 346, and 348 to a portion of the seat box 336 that has a conducive surface feature, as shown in FIG. 37B. In one embodiment, the conductive surface feature of the seat box 336 includes a foil tape 376 that contacts at least a portion of the surface 380 of the seat box 336, and forms a capacitive connection at least between the sinuous wires 342, 344, 346, and 348, the connection clips 358, 360, 362, and 364, and the bridging wire 324. As such, user occupancy information may be provided from the array of sinuous wires to the control component 320 via the bridging wire 324.

In FIG. 38, a perspective view 382 of a control component 320 for an automated recliner is provided, in accordance with embodiments of the invention. The control component 320 may be coupled to one or more conductive features of the recliner 296, such as to the base 314. In another aspect, the control component 320 may be coupled to additional/alternative conductive features of the recliner 296, such as coupling to the linkage 316. In the example of FIG. 38, the control component 320 may be coupled to the base 314 of the recliner 296 using conductive connection 326. Further, the control component 320 may be coupled to the base 314 via the wire connection 386. In some aspects of the invention, the control component 320 receives presence detection indications via the wire connection 386 and/or conductive connection 326 coupling the control component into one or more conductive features of the recliner 296, such as the base 314. In further aspects, the control component receives occupancy detection with respect to the top seat surface (i.e., whether a user is seated or not) from the bridging wire 324 coupled to the sinuous wires 342, 344, 346, 348 adjacent the eat bottom surface 354.

Figure 39:
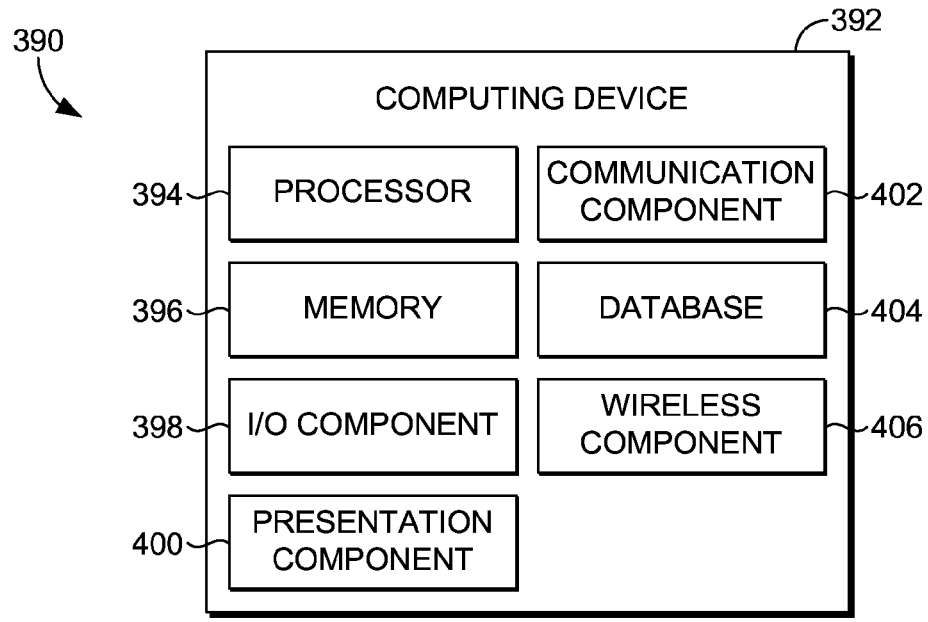
FIG. 39 is a system diagram of a computing device configured to interact with embodiments of the present invention.

Turning now to FIG. 39, a system diagram 390 of a computing device 392 is depicted according to one embodiment of the present invention. The computing device 392 may include one or more of the following components: a processor 394, a memory 396, an input/output component 398, a communication component 402, a database 404, and a wireless component 406. Based on utilizing one or more computing devices 392 with embodiments of the invention, a determination may be made as to what types of sensor detection is received by the control component 320, such as a capacitive detection of presence underneath and/or behind an articulating, automated recliner 296, or an occupancy detection of a user seated on the seat top surface 322.

Figure 40:
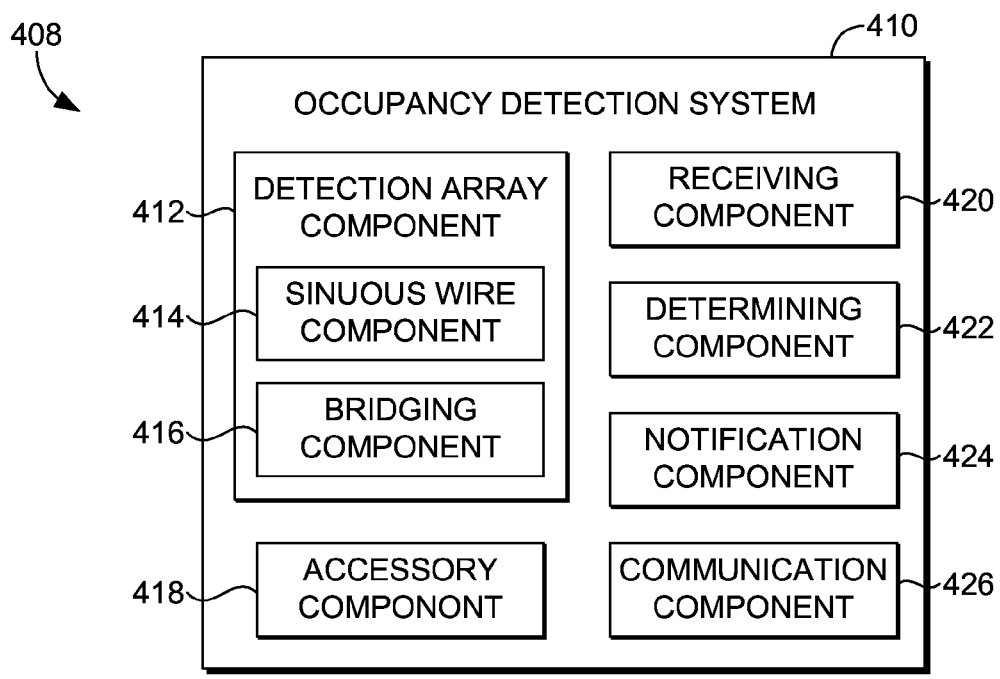
FIG. 40 is a system diagram of occupancy detection components for a sinuous wire detection array, in accordance with embodiments of the invention.

As shown in further detail in FIG. 40, a system diagram 408 of occupancy detection components for a sinuous wire detection array is provided, in accordance with embodiments of the invention. The exemplary occupancy detection system 410 includes a detection array component 412 having a sinuous wire component 414 and a bridging component 416, an accessory component 418, a receiving component 420, a determining component 422, a notification component 424, and a communication component 426. In embodiments, one or more of the components of the occupancy detection system 410 may be combined into a single component that performs the tasks of multiple components depicted in FIG. 40. For example, a single control component may include the features of the receiving component 420, determining component 422, and notification component 424. The detection array component 412 may include one or more sinuous wires coupled to at least a portion of a recliner seat, as part of the sinuous wire component 414. Further, each of the sinuous wires in sinuous wire component 414 may be coupled together as a capacitive sensor based on coupling to the bridging component 416. In one aspect, the bridging component 416 includes a bridging wire 324. In another aspect, the bridging component 416 includes a foil tape 376, or other capacitive surface feature on a surface 380 of the seat box 336.

According to one embodiment, the receiving component 420 may receive an indication of user occupancy of the recliner 296 based on information collected via the sinuous wires 342, 344, 346, and/or 348. By detecting an amount of change in capacitance via the series/set of sinuous wires, the capacitive array formed among the sinuous wires serves as an occupancy detector that may trigger one or more additional functions/features of a seating device, such as an automated recliner 296. For example, occupancy detection via sinuous wires may be used in a theatre setting to determine when to illuminate walkway safety lighting when an occupant exits a seat, via accessory component 418. In another example, the notification component 424 may indicate to a service provider, such as a hospital staff member, that an occupant has exited a seat surface via an occupancy detection system 410 monitoring whether a patient has exited a particular chair having a sinuous wire array.

Figure 41:
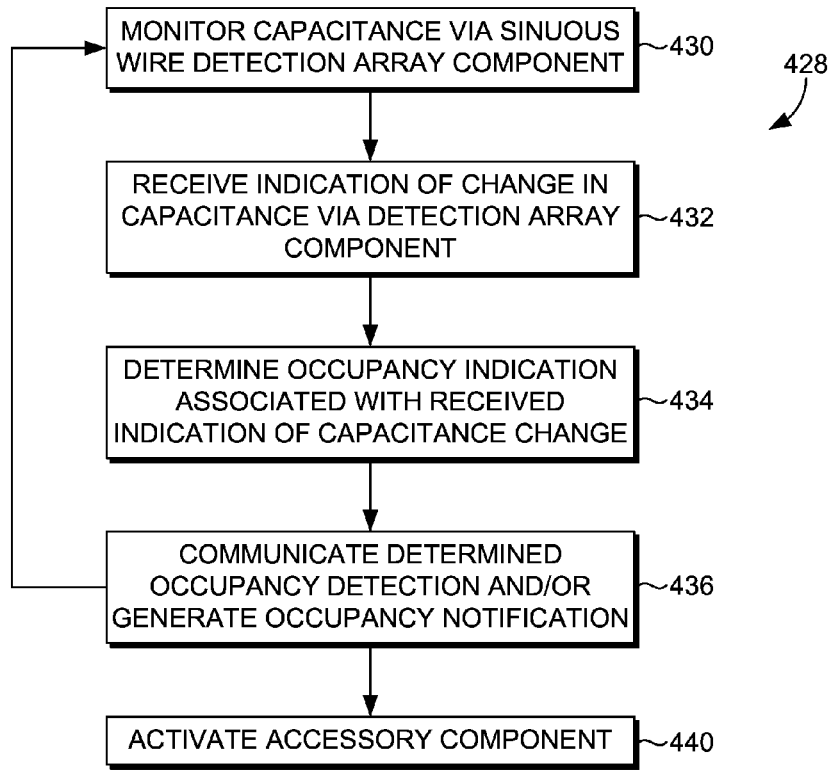
FIG. 41 is a flow diagram of a method of monitoring capacitance via the sinuous wire detection array.

Turning now to FIG. 41, a flow diagram 41 of a method of monitoring capacitance via the sinuous wire detection array for occupancy detection is provided. At block 430, capacitance is monitored via sinuous wire detection array component 412. At block 432, an indication of change in capacitance is received via the detection array component 412. Such an indication of change in capacitance may include a user sitting down on a seat surface, or a user exiting a seat surface. At block 434, the corresponding occupancy indication associated with the received indication of capacitance change is determined. Such determination may include identifying whether a user has temporarily or permanently exited a seating surface, whether a user has shifted in their seat to trigger a non-alerting change in capacitance, and/or whether occupancy has changed at a time when other features of the chair are not permitted to function (e.g., a user may be required to be seated in the chair in order for the lift features to raise/lower/tilt the automated recliner 296).

At block 436, the determined occupancy detection may be communicated to a control component and/or an occupancy notification may be generated. For example, the determined occupancy indication may be communicated to a control component of the automated recliner 296 for activation/inactivation of one or more functions of the recliner 296. In another embodiment, the system may communicate an indication of occupancy change to an external source, such as to a room monitor in a theater seating environment or a hospital seating system. Upon communicating the occupancy detection or generated occupancy notification at block 436, the system may continue monitoring capacitance vie the sinuous wire detection array component at block 430.

Additionally or alternatively, at block 440, one or more accessory component may be activated in response to the communicated determined occupancy or the generated occupancy notification. For example, a series of lights may be illuminated in response to a determination that one or more occupants have exited a seating system. In further aspects, an accessory such as a room light or nurse's station alert may indicate to a common monitoring system that a particular occupant has exited a seat utilizing sinuous wire detection.

Figure 42:
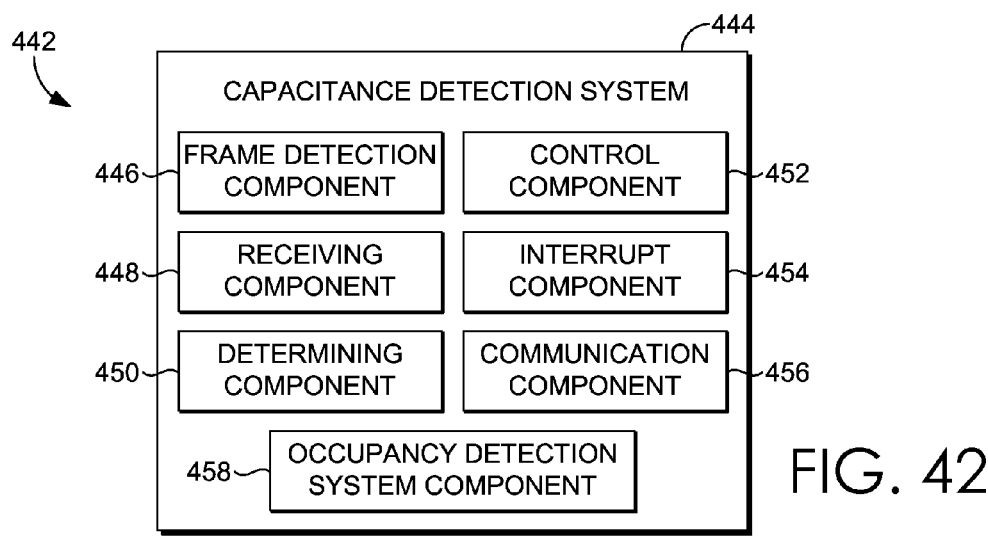
FIG. 42 is a system diagram of capacitance detection components for a frame detection system, in accordance with embodiments of the invention.

In FIG. 42, a system diagram 442 of capacitance detection components for a frame detection system is provided in accordance with embodiments of the invention. The capacitance detection system 444 includes a frame detection component 446, a receiving component 448, a determining component 450, a control component 452, an interrupt component 454, a communication component 456, and an occupancy detection system component 458. One or more features of the capacitance detection system 444 may be utilized to activate or inactive one or more features of an automated recliner 296. For example, the frame detection component 446 may receive information including a threshold change in capacitance from receiving component 448, which is analyzed by determining component 450 to determine whether a detected change in capacitance does or does satisfy a threshold change in capacitance that triggers a particular response. The interrupt component 454 may be engaged to interrupt travel of the automated recliner 296 when the frame detection component 446 monitors for a change in capacitance that the receiving component 448 receives and the determining component 450 determines to have satisfied a threshold for indicating that a person is in contact with a portion of the automated recliner 296.

Also included within the exemplary capacitance detection system 44 is the occupancy detection system component 458, which may provide an additional item of information to the capacitance detection system 444 when the determining component 450 is interpreting the received capacitance data. For example, the occupancy detection system component 458 may receive an indication that a user has been seated on the automated recliner 296. Upon being seated, overall capacitance detected by the frame detection component 446 may be insulated by the presence of the occupancy detection system component 458, and in particular, by the sinuous wire array detector. As such, a "false positive" for detection of presence underneath a recliner 296 may be disengaged based on confirming that the spike in capacitive detection experience by the frame detection component 446 actually corresponds to a user sitting down on the recliner body 298 and/or seat surface 322.

Figure 43:
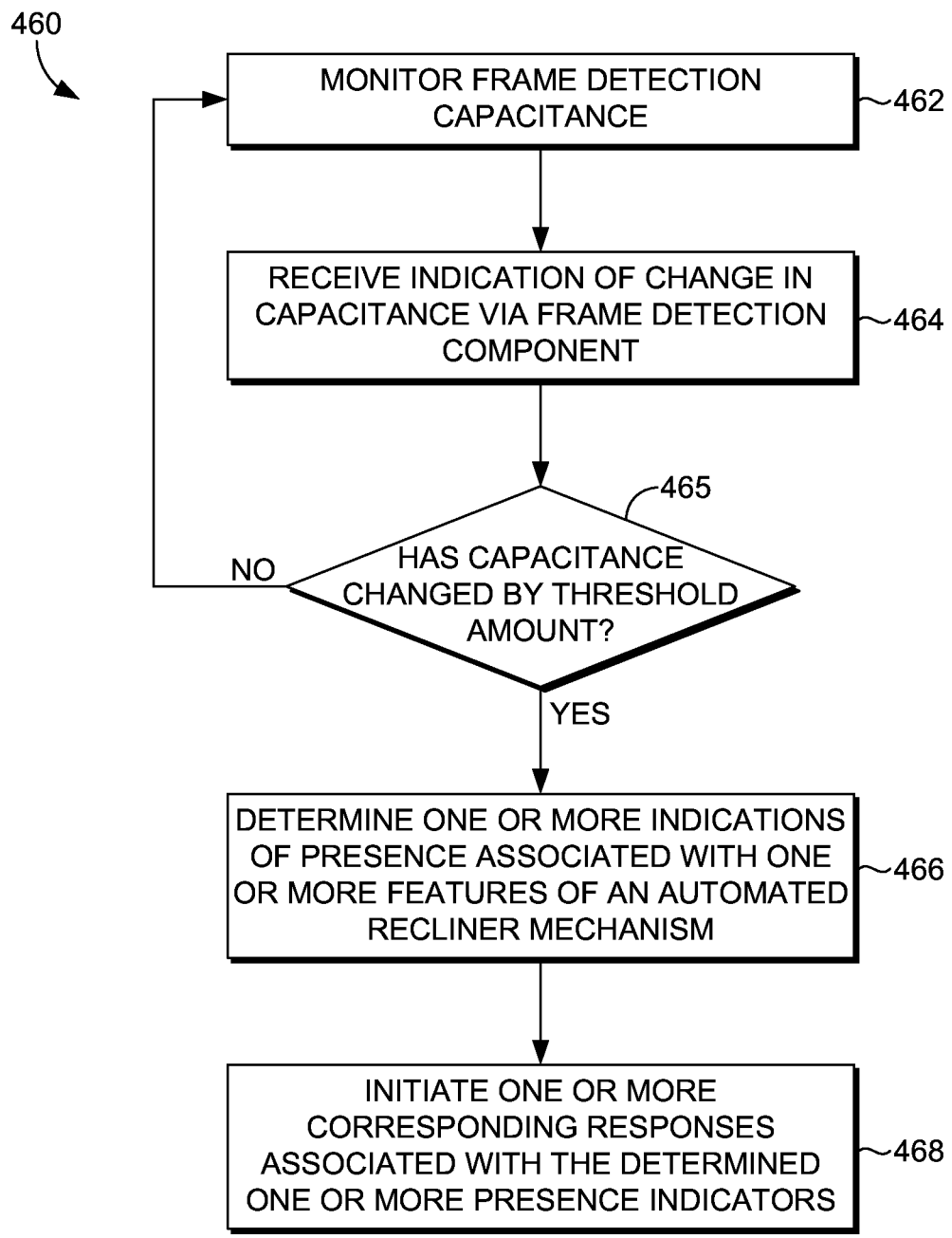
FIG. 43 is a flow diagram of a method for monitoring capacitance via the frame detection component.

Turning next to FIG. 43, a flow diagram 460 of a method for monitoring capacitance via the frame detection component is provided according to an embodiment of the invention. At block 462, frame detection capacitance is monitored, as discussed above. At block 464, an indication of a change in capacitance is received via frame detection component. Further, at block 465, a determination is made whether the detected change in capacitance has satisfied a threshold amount. If the threshold amount of change in capacitance is not satisfied at block 465, the method returns to block 462 for continued monitoring. If a threshold amount of capacitance change is determined at block 465, the method continues to block 466, where one or more indications of presence associated with one or more features of an automated recliner mechanism are determined. Further, at block 468, one or more corresponding responses associated with the determined one or more presence indicators are initiated.

Figure 44:
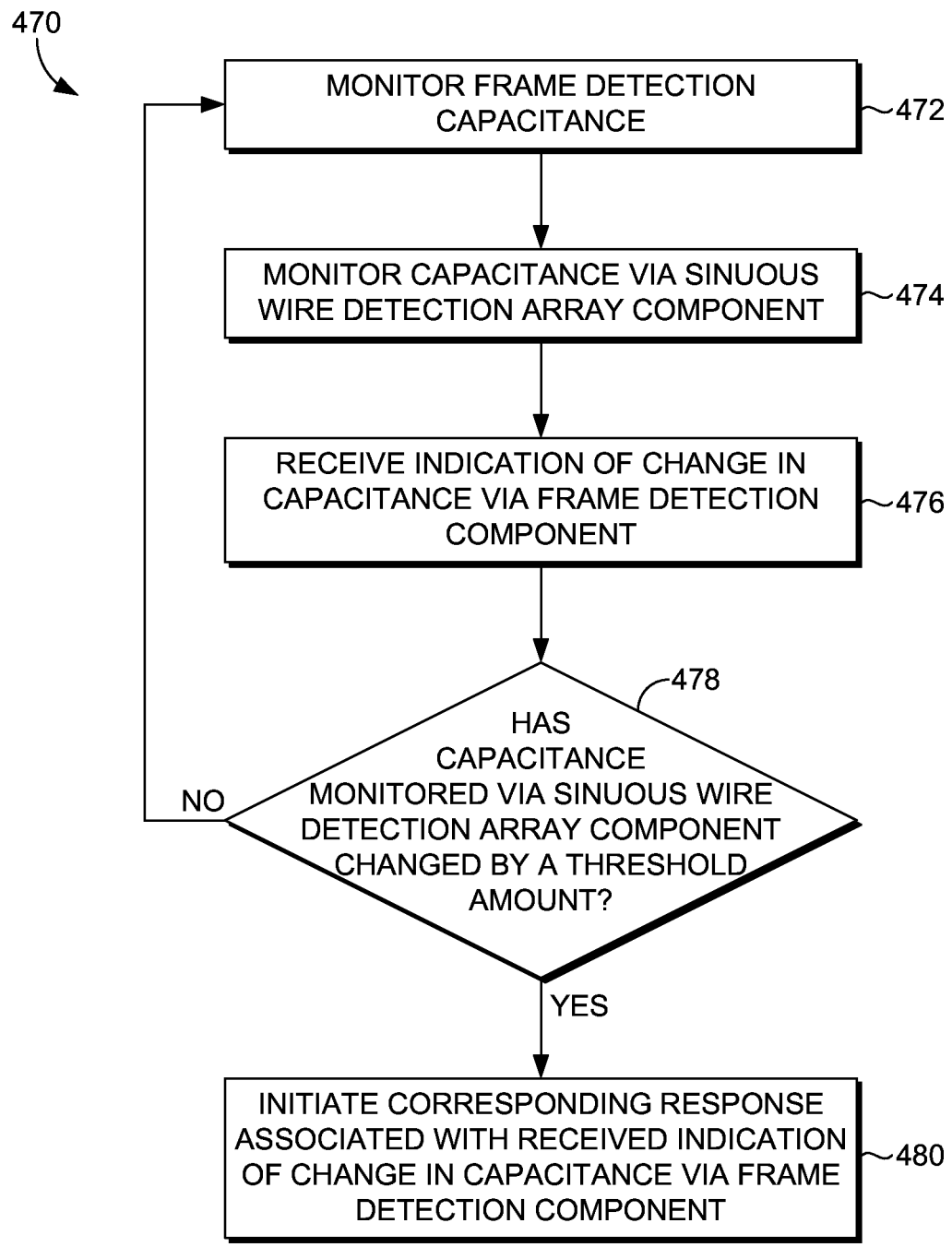
FIG. 44 is a flow diagram for a method of monitoring frame detection capacitance and sinuous wire detection array components, in accordance with embodiments of the invention.

Referring finally to FIG. 44, a flow diagram 470 for a method of monitoring frame detection capacitance and sinuous wire detection array components is provided in accordance with embodiments of the invention. AT block 472, frame detection capacitance is monitored. AT block 474, capacitance via sinuous wire detection array component is monitored. Accordingly, at block 476, an indication of change in capacitance via the frame detection component is received. AT block 478, a determination is made whether the capacitance monitored via sinuous wire detection array component has changed by a threshold amount. For example, the change in capacitance via frame detection component received at block 476 may indicate a "false positive" for presence beneath an automated recliner 296. As such, the monitored sinuous wire detection array capacitance data from block 474 may be used to determine if a user has, within a threshold amount of time and/or with a threshold change in capacitance, entered the recliner 296. If the capacitance monitored by the sinuous wire detection array component has not changed by a threshold amount, monitoring by the frame detection component returns to block 472. If capacitance monitored by the sinuous wire detection array component has changed by a threshold amount, a corresponding response is initiated associated with the received indication of change in capacitance via the frame detection component at block 480.

For example, a threshold for sinuous wire detection at block 478 may identify an amount of change in capacitance detection that is attributed to a change in occupancy, rather than a change in presence detection with respect to the recliner 296. If the change in capacitance does not satisfy a threshold indication of presence (e.g., an indication of detection from the sinuous wire detection array that identifies occupancy alone), then the method may continue to monitor capacitance at block 472. If the change in capacitance does satisfy a threshold indication of presence (e.g., an indication of detection from the sinuous wire detection array that does not indicate that the change in occupancy is attributed to occupancy, rather than presence), the corresponding response may be initiated at block 480.

From the foregoing, it will be seen that this invention is one well adapted to attain all the ends and objects hereinabove set forth together with other advantages, which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

The invention claimed is:

1. A presence detection system comprising:
an automated furniture item comprising a frame detection component, wherein the frame detection component comprises:
(1) a first conductive furniture feature comprising at least one conductive frame member of the furniture item, wherein the conductive frame member is configured to have a voltage based on proximity of an object to the conductive frame member, and (2) a second conductive furniture feature coupled to the first conductive furniture feature, the second conductive furniture feature comprising at least one articulating furniture feature; and a control component coupled to the frame detection component, the control component comprising:

(1) a receiving component configured to receive at least one indication of change in capacitance from the frame detection component, wherein the control component is configured to monitor a change in capacitance with respect to the frame detection component; and (2) a determining component configured to determine whether the received at least one indication of the change in capacitance over time satisfies a threshold change in capacitance over a threshold period of time.

2. The presence detection system of claim 1, wherein upon determining that the received at least one indication of change in capacitance satisfies the threshold change in capacitance, the determining component is configured to generate an indication of presence detection.

3. The presence detection system of claim 1, further comprising one or more of:

an interrupt component configured to activate or inactivate one or more automated features of the automated furniture item;

a communication component configured to communicate a determination of presence to one or more users; and an occupancy detection system component configured to provide an indication of occupancy of the automated furniture item to the presence detection system.

4. The presence detection system of claim 3, wherein the communication component comprises a wireless component.

5. A method for detecting presence with respect to an automated recliner, the method comprising:

receiving capacitance monitoring data from a frame detection component comprising at least one conductive frame member coupled to the automated furniture, wherein the conductive frame member is configured to have a voltage based on proximity of an object to the conductive frame member, and further wherein the frame detection component comprises one or more conductive features associated with the automated recliner that couple together to provide a capacitive sensor frame; and determining that the change in voltage satisfies a threshold, wherein determining that the change in voltage satisfies a threshold comprises:

(1) monitoring rate of change in voltage detected by the frame detection component; and (2) comparing the rate of change in voltage with the threshold.

6. The method of claim 5, further comprising, based on determining that the change in voltage satisfies a threshold, activating or deactivating or more features associated with the automated recliner.

7. The method of claim 5, further comprising, upon determining that the change in voltage satisfies a threshold, receiving an indication of occupancy detection via a sinuous wire detection array component of the automated recliner.

8. The method of claim 7, further comprising initiating a corresponding response associated with the received indication of occupancy detection and the determination that the change in voltage satisfies a threshold.

9. The method of claim 8, wherein the frame detection component is coupled to the control component of the automated recliner via a conductive connection configured to carry an indication of capacitance from the frame detection component to the control component.

10. A presence detection mechanism associated with an automated recliner, the presence detection mechanism comprising:

a capacitive sensing frame detection component comprising at least one conductive frame member configured to carry a charge, the capacitive sensing frame detection component comprising at least one stationary frame component of the automated recliner and at least one articulating frame component of the automated recliner, the at least one articulating frame component capacitively coupled to the at least one stationary frame component, said at least one articulating frame component configured to move at least between a first position and a second position;

a control component directly coupled to the capacitive sensing frame detection component, said control component configured to receive data associated with a monitored change in capacitance associated with the capacitive sensing frame detection component; and a determining component associated with the control component, said determining component configured to determine, based on the received data associated with a monitored change in capacitance, whether presence is detected in proximity to at least a portion of the automated recliner.

11. The presence detection mechanism of claim 10, wherein one or more of the determining component and the control component coupled to capacitive sensing frame detection component is configured to generate an indication that a change in voltage satisfies a threshold amount.

12. The presence detection mechanism of claim 11, wherein based on determining that the threshold amount is satisfied, initiating a corresponding response.

13. The presence detection mechanism of claim 12, further comprising:

an interrupt component configured to activate or deactivate the at least one articulating frame component based on a determined indication of presence.

14. The presence detection mechanism of claim 13, wherein the deactivating the at least one articulating frame component comprises discontinuing movement between the first position and the second position.

15. The presence detection mechanism of claim 13, wherein upon deactivating the at least one articulating frame component, the control component is configured to deactivate one or more additional features of the automated recliner while data received from the capacitive sensing frame detection component indicates occupancy.

16. The presence detection mechanism of claim 15, wherein the one or more additional features of the automated recliner remain deactivated until manual user input of an indication presence is no longer detected with respect to the at least one articulating frame component.

17. The presence detection mechanism of claim 16, wherein the automated recliner comprises an automated recliner control coupled to the control component, wherein the automated recliner control is configured to receive user input of the indication that presence is no longer detected with respect to the at least one articulating frame component.

18. The presence detection mechanism of claim 10, wherein the capacitive sensing frame detection component of claim 10 is configured to monitor a change in capacitance during movement of the automated recliner from a first lowered position to a second raised position, wherein upon detection of presence with respect to at least a portion of the capacitive sensing frame detection component, the movement of one or more articulating features of the automated recliner are deactivated.

* * * * *